(12) United States Patent
Kim et al.

(10) Patent No.: US 11,396,453 B2
(45) Date of Patent: Jul. 26, 2022

(54) METAL COMPOUND HAVING PHASE TRANSFORMATION AND METHOD OF PREPARING THE SAME

(71) Applicant: WEBIOTREE CO., LTD, Seoul (KR)

(72) Inventors: Ho Jun Kim, Seoul (KR); Ki Yeok Kim, Seoul (KR)

(73) Assignee: WEBIOTREE CO.. LTD, Seoul (KR)

( * ) Notice: Subject to any disclaimer, the term of this patent is extended or adjusted under 35 U.S.C. 154(b) by 0 days.

(21) Appl. No.: 17/424,071

(22) PCT Filed: Mar. 10, 2021

(86) PCT No.: PCT/KR2021/002959
§ 371 (c)(1),
(2) Date: Jul. 19, 2021

(87) PCT Pub. No.: WO2021/246620
PCT Pub. Date: Dec. 9, 2021

(65) Prior Publication Data
US 2022/0041461 A1    Feb. 10, 2022

(30) Foreign Application Priority Data

Jun. 2, 2020  (KR) .................. 10-2020-0066600

(51) Int. Cl.
| | |
|---|---|
| C07F 3/06 | (2006.01) |
| C07F 3/02 | (2006.01) |
| C07F 3/04 | (2006.01) |
| C07F 1/08 | (2006.01) |
| C07F 15/06 | (2006.01) |
| C07F 15/04 | (2006.01) |
| C01G 9/02 | (2006.01) |
| C01G 3/02 | (2006.01) |
| C01G 51/04 | (2006.01) |
| C01G 53/04 | (2006.01) |
| A61K 33/30 | (2006.01) |
| A61K 33/08 | (2006.01) |
| A61K 33/34 | (2006.01) |
| A61K 33/24 | (2019.01) |
| A61K 38/06 | (2006.01) |
| A61K 38/05 | (2006.01) |
| A61K 38/07 | (2006.01) |
| A61K 38/08 | (2019.01) |
| A61K 9/14 | (2006.01) |

(52) U.S. Cl.
CPC ............. $C01G\ 9/02$ (2013.01); $A61K\ 9/143$ (2013.01); $A61K\ 38/06$ (2013.01); $C01P\ 2002/72$ (2013.01)

(58) Field of Classification Search
CPC ...... C07F 3/06; C07F 3/02; C07F 3/04; C07F 1/08; C07F 15/065; C07F 15/06; C07F 15/045; C07F 15/04; C01G 9/02; C01G 3/02; C01G 51/04; C01G 53/04; A61K 33/30; A61K 33/08; A61K 33/34; A61K 33/24; A61K 38/06; A61K 38/05; A61K 38/07; A61K 38/08
USPC ........... 514/494, 499, 501, 21.91, 21.9, 21.7, 514/21.8
See application file for complete search history.

(56) References Cited

U.S. PATENT DOCUMENTS

2008/0031966 A1    2/2008  Tzannis

FOREIGN PATENT DOCUMENTS

| | | | |
|---|---|---|---|
| KR | 10-2019-0075838 A | 7/2019 | |
| KR | 10-2020-0040144 A | 4/2020 | |
| KR | 10-2020-0040143 A | 6/2020 | |
| WO | 2007-022239 A2 | 2/2007 | |
| WO | WO-2011126382 A1 * | 10/2011 | ............... C10G 1/08 |

OTHER PUBLICATIONS

Xiaoling Wu et al., "Packaging and delivering enzymes by amorphous metal-organic frameworks", Nature, Nature Communications, 2019.
International search report for PCT/KR2021/002959 dated Jun. 14, 2021.
Notification of Reason for Refusal issued by Korean Patent Office in counterpart Korean Application No. 10-2020-0066600 dated Jan. 11, 2021.
Grant of Patent issued by Korean Patent Office in counterpart Korean Application No. 10-2020-0066600 dated Feb. 19, 2021.

* cited by examiner

*Primary Examiner* — Joseph R Kosack
*Assistant Examiner* — Sagar Patel
(74) *Attorney, Agent, or Firm* — Sughrue Mion, PLLC

(57) ABSTRACT

The present invention relates to a metal phase transformation compound and a method for preparing the same.

8 Claims, 24 Drawing Sheets
Specification includes a Sequence Listing.

SEQUENCE LISTING

<160> NUMBER OF SEQ ID NOS: 40

<210> SEQ ID NO 1
<211> LENGTH: 4
<212> TYPE: PRT
<213> ORGANISM: Artificial sequence

```
<220> FEATURE:
<223> OTHER INFORMATION: RKR peptide

<400> SEQUENCE: 1

Arg Lys Arg Met
1

<210> SEQ ID NO 2
<211> LENGTH: 4
<212> TYPE: PRT
<213> ORGANISM: Artificial sequence
<220> FEATURE:
<223> OTHER INFORMATION: tetrapeptide-1

<400> SEQUENCE: 2

Leu Pro Thr Val
1

<210> SEQ ID NO 3
<211> LENGTH: 4
<212> TYPE: PRT
<213> ORGANISM: Artificial sequence
<220> FEATURE:
<223> OTHER INFORMATION: tetrapeptide-2

<400> SEQUENCE: 3

Lys Asp Val Tyr
1

<210> SEQ ID NO 4
<211> LENGTH: 4
<212> TYPE: PRT
<213> ORGANISM: Artificial sequence
<220> FEATURE:
<223> OTHER INFORMATION: tetrapeptide-3

<400> SEQUENCE: 4

Lys Gly His Lys
1

<210> SEQ ID NO 5
<211> LENGTH: 4
<212> TYPE: PRT
<213> ORGANISM: Artificial sequence
<220> FEATURE:
<223> OTHER INFORMATION: tetrapeptide-5

<400> SEQUENCE: 5

Ala His Ser His
1

<210> SEQ ID NO 6
<211> LENGTH: 4
<212> TYPE: PRT
<213> ORGANISM: Artificial sequence
<220> FEATURE:
<223> OTHER INFORMATION: tetrapeptide-7

<400> SEQUENCE: 6

Gly Gln Pro Arg
1

<210> SEQ ID NO 7
<211> LENGTH: 4
<212> TYPE: PRT
<213> ORGANISM: Artificial sequence
<220> FEATURE:
```

```
<223> OTHER INFORMATION: tetrapeptide-9

<400> SEQUENCE: 7

Gln Asp Val His
1

<210> SEQ ID NO 8
<211> LENGTH: 4
<212> TYPE: PRT
<213> ORGANISM: Artificial sequence
<220> FEATURE:
<223> OTHER INFORMATION: tetrapeptide-11

<400> SEQUENCE: 8

Pro Pro Tyr Leu
1

<210> SEQ ID NO 9
<211> LENGTH: 4
<212> TYPE: PRT
<213> ORGANISM: Artificial sequence
<220> FEATURE:
<223> OTHER INFORMATION: tetrapeptide-15

<400> SEQUENCE: 9

Tyr Pro Phe Phe
1

<210> SEQ ID NO 10
<211> LENGTH: 4
<212> TYPE: PRT
<213> ORGANISM: Artificial sequence
<220> FEATURE:
<223> OTHER INFORMATION: tetrapeptide-21

<400> SEQUENCE: 10

Gly Glu Lys Gly
1

<210> SEQ ID NO 11
<211> LENGTH: 4
<212> TYPE: PRT
<213> ORGANISM: Artificial sequence
<220> FEATURE:
<223> OTHER INFORMATION: tetrapeptide-26

<400> SEQUENCE: 11

Glu Leu Pro Ser
1

<210> SEQ ID NO 12
<211> LENGTH: 4
<212> TYPE: PRT
<213> ORGANISM: Artificial sequence
<220> FEATURE:
<223> OTHER INFORMATION: acetyl tetrapeptide-2

<400> SEQUENCE: 12

Lys Asp Val Tyr
1

<210> SEQ ID NO 13
<211> LENGTH: 4
<212> TYPE: PRT
<213> ORGANISM: Artificial sequence
<220> FEATURE:
<223> OTHER INFORMATION: acetyl tetrapeptide-3
```

```
<400> SEQUENCE: 13

Lys Gly His Lys
1

<210> SEQ ID NO 14
<211> LENGTH: 4
<212> TYPE: PRT
<213> ORGANISM: Artificial sequence
<220> FEATURE:
<223> OTHER INFORMATION: tetrapeptide-5

<400> SEQUENCE: 14

Ala His Ser His
1

<210> SEQ ID NO 15
<211> LENGTH: 4
<212> TYPE: PRT
<213> ORGANISM: Artificial sequence
<220> FEATURE:
<223> OTHER INFORMATION: acetyl tetrapeptide-9

<400> SEQUENCE: 15

Gln Asp Val His
1

<210> SEQ ID NO 16
<211> LENGTH: 4
<212> TYPE: PRT
<213> ORGANISM: Artificial sequence
<220> FEATURE:
<223> OTHER INFORMATION: acetyl tetrapeptide-11

<400> SEQUENCE: 16

Pro Pro Tyr Leu
1

<210> SEQ ID NO 17
<211> LENGTH: 4
<212> TYPE: PRT
<213> ORGANISM: Artificial sequence
<220> FEATURE:
<223> OTHER INFORMATION: acetyl tetrapeptide-15

<400> SEQUENCE: 17

Tyr Pro Phe Phe
1

<210> SEQ ID NO 18
<211> LENGTH: 5
<212> TYPE: PRT
<213> ORGANISM: Artificial sequence
<220> FEATURE:
<223> OTHER INFORMATION: pentapeptide-3

<400> SEQUENCE: 18

Gly Pro Arg Pro Ala
1               5

<210> SEQ ID NO 19
<211> LENGTH: 5
<212> TYPE: PRT
<213> ORGANISM: Artificial sequence
<220> FEATURE:
<223> OTHER INFORMATION: pentapeptide-4
```

```
<400> SEQUENCE: 19

Lys Thr Thr Lys Ser
1               5

<210> SEQ ID NO 20
<211> LENGTH: 5
<212> TYPE: PRT
<213> ORGANISM: Artificial sequence
<220> FEATURE:
<223> OTHER INFORMATION: pentapeptide-17

<400> SEQUENCE: 20

Lys Leu Ala Lys Lys
1               5

<210> SEQ ID NO 21
<211> LENGTH: 5
<212> TYPE: PRT
<213> ORGANISM: Artificial sequence
<220> FEATURE:
<223> OTHER INFORMATION: pentapeptide-18

<400> SEQUENCE: 21

Tyr Ala Gly Phe Leu
1               5

<210> SEQ ID NO 22
<211> LENGTH: 5
<212> TYPE: PRT
<213> ORGANISM: Artificial sequence
<220> FEATURE:
<223> OTHER INFORMATION: thioctoyl pentapeptide-4

<400> SEQUENCE: 22

Lys Thr Thr Lys Ser
1               5

<210> SEQ ID NO 23
<211> LENGTH: 6
<212> TYPE: PRT
<213> ORGANISM: Artificial sequence
<220> FEATURE:
<223> OTHER INFORMATION: hexapeptide-1

<400> SEQUENCE: 23

Ala Arg His Leu Phe Trp
1               5

<210> SEQ ID NO 24
<211> LENGTH: 6
<212> TYPE: PRT
<213> ORGANISM: Artificial sequence
<220> FEATURE:
<223> OTHER INFORMATION: hexapeptide-2

<400> SEQUENCE: 24

Phe Trp Phe Lys Pro Val
1               5

<210> SEQ ID NO 25
<211> LENGTH: 6
<212> TYPE: PRT
<213> ORGANISM: Artificial sequence
<220> FEATURE:
<223> OTHER INFORMATION: hexapeptide-3

<400> SEQUENCE: 25
```

```
Glu Glu Met Gln Arg Arg
1               5

<210> SEQ ID NO 26
<211> LENGTH: 6
<212> TYPE: PRT
<213> ORGANISM: Artificial sequence
<220> FEATURE:
<223> OTHER INFORMATION: hexapeptide-4
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Phe Gly His Xaa Ala Phe
1               5

<210> SEQ ID NO 27
<211> LENGTH: 6
<212> TYPE: PRT
<213> ORGANISM: Artificial sequence
<220> FEATURE:
<223> OTHER INFORMATION: hexapeptide-5
<220> FEATURE:
<221> NAME/KEY: misc_feature
<222> LOCATION: (4)..(4)
<223> OTHER INFORMATION: Xaa can be any naturally occurring amino acid

<400> SEQUENCE: 27

Phe Gly Val Xaa Ala Phe
1               5

<210> SEQ ID NO 28
<211> LENGTH: 6
<212> TYPE: PRT
<213> ORGANISM: Artificial sequence
<220> FEATURE:
<223> OTHER INFORMATION: hexapeptide-6

<400> SEQUENCE: 28

Val Glu Pro Ile Pro Tyr
1               5

<210> SEQ ID NO 29
<211> LENGTH: 6
<212> TYPE: PRT
<213> ORGANISM: Artificial sequence
<220> FEATURE:
<223> OTHER INFORMATION: hexapeptide-9

<400> SEQUENCE: 29

Gly Pro Gln Gly Pro Gln
1               5

<210> SEQ ID NO 30
<211> LENGTH: 6
<212> TYPE: PRT
<213> ORGANISM: Artificial sequence
<220> FEATURE:
<223> OTHER INFORMATION: hexapeptide-11

<400> SEQUENCE: 30

Phe Val Ala Pro Phe Pro
1               5

<210> SEQ ID NO 31
```

```
<211> LENGTH: 6
<212> TYPE: PRT
<213> ORGANISM: Artificial sequence
<220> FEATURE:
<223> OTHER INFORMATION: hexapeptide-12

<400> SEQUENCE: 31

Val Gly Val Ala Pro Gly
1               5

<210> SEQ ID NO 32
<211> LENGTH: 6
<212> TYPE: PRT
<213> ORGANISM: Artificial sequence
<220> FEATURE:
<223> OTHER INFORMATION: acetyl hexapeptide-3

<400> SEQUENCE: 32

Glu Glu Met Gln Arg Arg
1               5

<210> SEQ ID NO 33
<211> LENGTH: 6
<212> TYPE: PRT
<213> ORGANISM: Artificial sequence
<220> FEATURE:
<223> OTHER INFORMATION: acetyl hexapeptide-8

<400> SEQUENCE: 33

Glu Glu Met Gln Arg Arg
1               5

<210> SEQ ID NO 34
<211> LENGTH: 6
<212> TYPE: PRT
<213> ORGANISM: Artificial sequence
<220> FEATURE:
<223> OTHER INFORMATION: heptapeptide-6

<400> SEQUENCE: 34

His Trp Ala Trp Phe Lys
1               5

<210> SEQ ID NO 35
<211> LENGTH: 7
<212> TYPE: PRT
<213> ORGANISM: Artificial sequence
<220> FEATURE:
<223> OTHER INFORMATION: cysteine peptide

<400> SEQUENCE: 35

Arg Phe Ala Ala Cys Ala Ala
1               5

<210> SEQ ID NO 36
<211> LENGTH: 4
<212> TYPE: PRT
<213> ORGANISM: Artificial sequence
<220> FEATURE:
<223> OTHER INFORMATION: tetrapeptide-7

<400> SEQUENCE: 36

Gly Gln Pro Arg
1

<210> SEQ ID NO 37
<211> LENGTH: 5
```

```
<212> TYPE: PRT
<213> ORGANISM: Artificial sequence
<220> FEATURE:
<223> OTHER INFORMATION: myristoyl pentapeptide-17

<400> SEQUENCE: 37

Lys Leu Ala Lys Lys
1               5

<210> SEQ ID NO 38
<211> LENGTH: 5
<212> TYPE: PRT
<213> ORGANISM: Artificial sequence
<220> FEATURE:
<223> OTHER INFORMATION: palmitoyl pentapeptide-4

<400> SEQUENCE: 38

Lys Thr Thr Lys Ser
1               5

<210> SEQ ID NO 39
<211> LENGTH: 5
<212> TYPE: PRT
<213> ORGANISM: Artificial sequence
<220> FEATURE:
<223> OTHER INFORMATION: palmitoyl pentapeptide-17

<400> SEQUENCE: 39

Lys Leu Ala Lys Lys
1               5

<210> SEQ ID NO 40
<211> LENGTH: 6
<212> TYPE: PRT
<213> ORGANISM: Artificial sequence
<220> FEATURE:
<223> OTHER INFORMATION: myristoyl hexapeptide-12 or palmitoyl
      hexapeptide-12

<400> SEQUENCE: 40

Val Gly Val Ala Pro Gly
1               5
```

METAL COMPOUND HAVING PHASE TRANSFORMATION AND METHOD OF PREPARING THE SAME

CROSS-REFERENCE TO RELATED APPLICATIONS

This application is a National Stage of International Application No. PCT/KR2021/002959 filed Mar. 10, 2021, which claims priority to Korean Patent Application No. 10-2020-0066600 filed on Jun. 2, 2020, the entire disclosures of which are incorporated herein by reference.

REFERENCE TO SEQUENCE LISTING

The Sequence Listing submitted as a text file named "Q265694 sequence listing as filed" having a size of 6.74 KB is hereby incorporated by reference pursuant to 37 C.F.R. § 1.52(e)(5).

TECHNICAL FIELD

The present invention relates to a metal compound having phase transformation and a method for preparing the same.

BACKGROUND ART

A material has its own crystal system, and its crystal habit changes depending on external conditions. Growth of the crystal face may be affected by external conditions, e.g., supersaturation, temperature, type of solvent, pH of solution, impurities, and stirring speed. That is, even materials of the same component may be crystallized into different shapes when external conditions are different, and can be largely divided into a crystalline form and an amorphous form according to an internal structure of the material. In the crystalline form, the constituent components in a unit cell, which is the basic constituent unit, are arranged in a certain arrangement to stabilize the crystal thermodynamically. Therefore, an active ingredient contained in a crystalline structure can be stably maintained, but dissolution is not easy, and thus in the case of the crystalline structure, it may be difficult to release the active ingredient (e.g., drug). On the other hand, in the case of an amorphous structure, the internal structure is arranged in a disorderly manner, and thus has relatively thermodynamically unstable characteristics, and the characteristics thereof are as follows.

i) Drugs in the amorphous structure can be dissolved and absorbed relatively easily compared to the crystalline form because there is no need to overcome lattice energy that appears in the crystalline form during dissolution. Therefore, the amorphous form has a relatively high equilibrium concentration (solubility) and has relatively excellent bioavailability (BA).

ii) The amorphous form is less stable than the crystalline form, but because it is a thermodynamically unstable material, it may crystallize naturally when left unattended.

iii) Drugs in the amorphous structure can be dissolved and absorbed relatively easily compared to the crystalline form because there is no need to overcome the lattice energy of the crystalline form during dissolution. Therefore, drugs contained in the amorphous structure generally exhibit higher solubility and a faster elution rate than the crystalline structure.

That is, in the case of a crystalline solid, the inter-elemental arrangement is arranged in a state with the lowest energy level, whereas in the case of an amorphous solid, the arrangement of the elements maintains an unstable state with a high energy level. Therefore, in the case of the same material, the crystalline solid is more chemically stable than the amorphous solid, and has low solubility and high density, and thus has the characteristics of attempting to maintain a thermodynamically stable crystalline form.

A metal compound such as zinc oxide or zinc hydroxide or an inorganic compound is a structure of solvates or hydrates with very high crystallinity, and the temperature, solvent, supersaturation, seed becoming/seed growth speed, crystallization mechanism, crystallization time, etc., during preparation act as main factors in crystal formation, and various such factors affect crystal creation. That is, conventional metal hydroxides have a very high crystallinity tendency, and thus it is difficult to form high amorphousness in a unit cell.

Conventionally, in relation to the metal hydroxide, there are a number of technologies related to metal hydroxides having a high proportion of crystalline form and nanocomposites using the same as in Korean Patent Registration No. 10-1738545, but metal hydroxides having high amorphousness cannot be found.

Accordingly, the present invention was devised to solve the problems described above.

DISCLOSURE OF THE INVENTION

Technical Problem

The present invention relates to a metal phase transformation compound having improved amorphousness in a metal compound, and to a metal phase transformation compound including both amorphousness and crystallinity. Specifically, the metal phase transformation compound of the present invention is a kind of drug carrier derived from the concept of drug delivery system (DDS), and has the characteristics of stably maintaining an unstable active ingredient and allowing the active ingredient to elute under certain conditions in an aqueous solution state.

Phase transformation in the present invention refers to a polymorph, and refers to a co-amorphous-crystalline metal compound including amorphousness and crystallinity in the metal compound in a composite manner. The metal phase transformation compound of the present invention has different physical properties from the crystalline compound in solubility, drug content, etc., and exhibits different characteristics from the existing crystalline form. The difference in physicochemical properties of polymorphic crystals is due to differences in orientation of and intermolecular interactions of adjacent molecules in the crystal structure, and the arrangement of constituent elements in the material also makes many differences in thermodynamic energy stability in a solid phase.

An object of the present invention is to provide a metal compound having characteristics of both amorphousness and crystallinity of the metal compound in one unit cell, and more specifically, a metal phase transformation compound including the co-amorphous-crystalline in which a crystal phase is in a state in which the amorphousness and the crystalline form are mixed in a complex manner by maximizing amorphousness.

Technical Solution

The present invention provides a metal phase transformation compound comprises peptides and, characterized in that it contains 60% by volume or more amorphous form.

Advantageous Effects

The metal phase transformation compound of the present invention has an effect capable of maximizing the content rate of an active ingredient, that is, peptides in the metal phase transformation compound by having a high ratio of amorphousness in the unit cell.

In addition, the metal phase transformation compound of the present invention simultaneously has crystallinity and amorphousness, and has an effect of stably carrying the active ingredient by having a high ratio of amorphousness, and also has an effect of excellent bioavailability, excellent solubility, and an excellent elution rate.

In addition, the present invention has an effect of providing a preparation invention capable of effectively forming a metal phase transformation compound having amorphousness.

MODE FOR CARRYING OUT THE INVENTION

Figure 1:
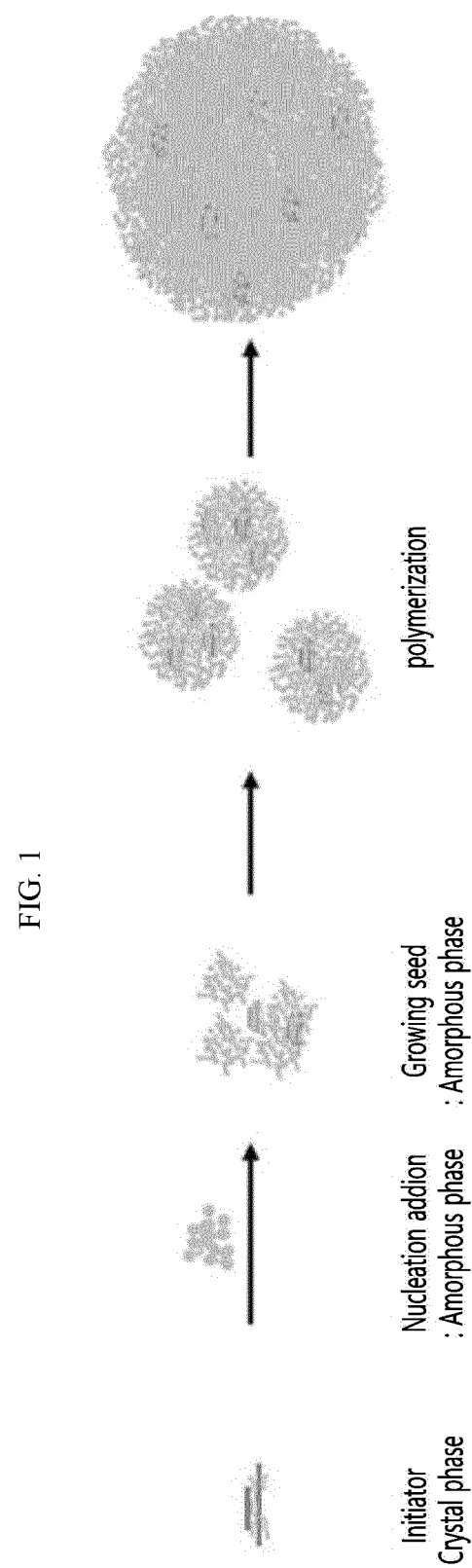
FIG. 1 is a scheme related to a method for forming a metal phase transformation compound of the present invention, and specifically, illustrates a process in which a portion of a coherent interface of a seed generated by nucleation is created and grown by movement of atoms in a particle according to growth of the crystalline phase and diffusional phase transformation. Accordingly, the initiation seed is stacked to form particles as a short-range order phase is formed and gradually increases along with a periodic order phase.
Figure 2:
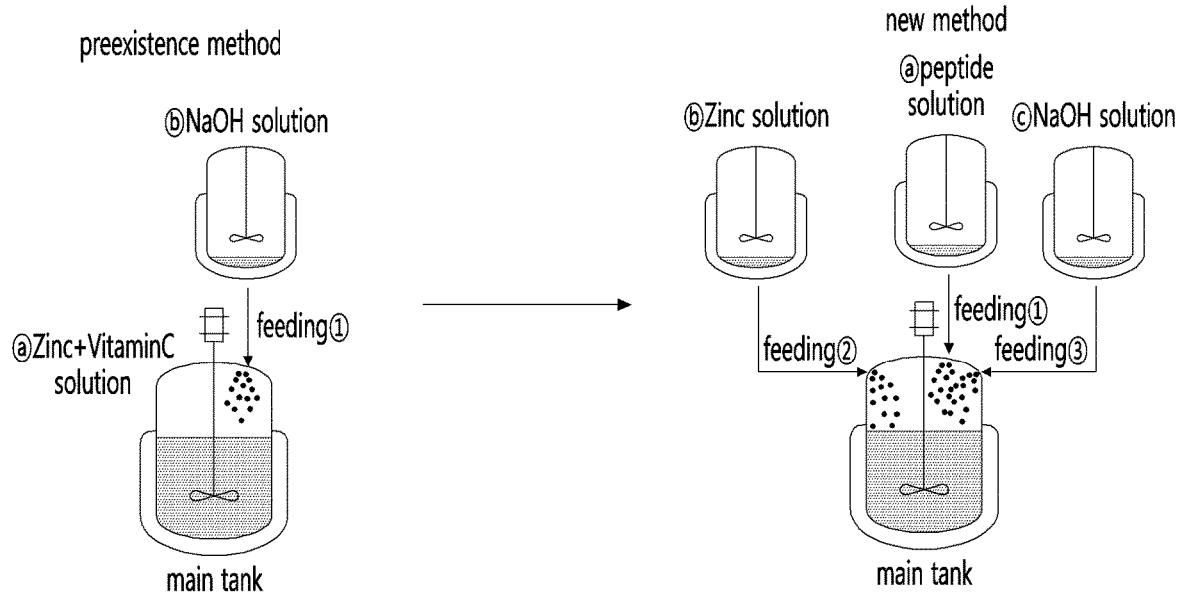
FIG. 2 is a schematic diagram of a conventional preexistence method illustrating a method for a metal hydroxide composite containing an active ingredient and a new method illustrating a method for preparing the metal phase transformation compound of the present invention.

The present invention increases amorphousness in the metal compound, thereby increasing increases the content of the active ingredient in the metal compound and allowing it to have excellent sustained-release properties. Typically, the metal compound has the characteristics of a crystallized metal compound with high crystallinity. Such a crystalline metal compound is a thermodynamically very stable material and has excellent crystallinity with excellent internal regularity. Regular deformation is induced in such a metal compound having high crystallinity by physicochemical methods to cause phase change and the derived heterocrystalline part (amorphous) is deposited with an anionic material to form the co Amorphous-Crystalline. In the case of the metal salt formed in this way, it is characterized in that the content of the active ingredient contained in the metal compound of the co amorphous-crystalline structure increases more than the content of the active ingredient of the original crystalline metal compound due to the change in the internal structure, the release amount of the active ingredient is controlled according to the pH change.

Specifically, the present invention relates to a metal phase transformation compound comprising a peptide, and characterized in that it contains 60% by volume or more amorphous form. That is, the present invention introduces amorphousness into the structure of existing limited metal compound to form a metal compound of a polymorph structure having characteristics of amorphousness and crystallinity at the same time. In the polymorphic structure, the chemical composition of material is the same, but molecules form different arrangements, and the polymorphic structure has characteristics of the crystal structure different from that of the existing metal compound because seeds grow due to physical forces, such as van der Waals forces, hydrogen bonding, and intermolecular interactions, acting differently to the seeds. In the present invention, a metal phase transformation compound having the co Amorphous-Crystalline in which the crystal phase is converted by artificially lowering the crystallinity to be changed into an amorphous structure by causing the distance between the atoms in contact with each other in the metal compound to be different by changing the symmetry and repeatability of the internal structure of the metal compound by using the polarity and solubility of the metal compound in the mixed solvent is devised.

Specifically, the metal phase transformation compound that may contain 1 to 40% by volume crystalline form and 99 to 60% by volume amorphous form, and preferably contains 1 to 35% by volume crystalline form and 99 to 65% by volume amorphous form, more preferably contains 1 to 30% by volume of crystalline form and 99 to 70% by volume amorphous form, still more preferably contains 1 to 25% by volume crystalline form and 99 to 75% by volume amorphous form, and still yet more preferably contains 1 to 15% by volume crystalline form and 99 to 85% by volume amorphous form is provided.

When the metal compound contains amorphousness in the above range, compared to a pure crystalline metal compound with low solubility due to thermodynamically stable atomic arrangement, a co-Amorphous-Crystalline metal phase transformation compound containing an active ingredient such as a peptide can adjust the particle size according to the pH and improve the release rate of the active ingredient contained therein. Furthermore, when the metal phase transformation compound is applied to a cosmetic formulation and then applied to the skin, it can be expected to improve the ability to fully deliver ingredients required to a user by a pH range (pH 4.5 to 7) of the skin.

The metal phase transformation compound of the present invention may specifically be a metal oxide or a metal hydroxide complex containing a peptide, which is not limited thereto, but preferably, may be expressed by the following chemical formula 1.

  [Chemical Formula 1]

(In Chemical Formula 1, $M^{2+}$ is $Mg^{2+}$, $Ca^{2+}$, $Co^{2+}$, $Cu^{2+}$, $Ni^{2+}$, or $Zn^{2+}$, A is physiologically active ingredients, x' is a number of 1 or more and less than 2;

y is a number of 0 or more and 2 or less;

z is a number of 0 or more and 2 or less, y+z does not exceed 2, y and z do not have a value of 0 at the same time, and n is a number of 0 or more and 10 or less).

In Chemical Formula 1, the physiologically active ingredients of A may be more preferable when they are peptides.

The peptides included in the present invention may be peptides having PI values of 2 to 12. The above peptides have a close relationship with pKa, and forms a coordinate covalent bond with metal ions at a pH of 5 to 10 or less, and in the above peptides, an activation site of the bonding active group, such as hydrogen bonding and carboxylate bonding, exhibits an effect of increasing amorphousness by the PI. Specifically, the peptides may be one or more peptides selected from dipeptide-1 (YR, (PI=, omitted hereinafter) 9.95), dipeptide-2 (VW, 5.98), dipeptide-4 (FW, 5.98), dipeptide-6 (KV, 9.07), dipeptide-7 (KT, 9.07), dipeptide-14 (AT, 5.98), GH dipeptide (GH, 7.37), acetyl dipeptide-1 (YR, 9.95), acetyl dipeptide-1 cetyl Ester (YR, 9.95), nicotinoyl dipeptide-2 (VW, 5.98), CP dipeptide (CP, 5.21), VGE dipeptide (VE, 3.64), CGE dipeptide (CE, 3.64), EGE dipeptide (EE, 3.46), TGE dipeptide (TE, 3.64), LGE dipeptide (LE, 3.64), EQ dipeptide (EQ, 3.64), GR dipeptide (GR, 10.47), HG dipeptide (HG, 7.37), PE dipeptide (PE, 3.64), DE dipeptide (DE, 3.29), HQ dipeptide (HQ, 7.37), RS dipeptide (RS, 10.47), HP dipeptide (HP, 7.37), carnosine (AH, 7.37), tipeptide-1 (GHK, 9.07), tripedide-3 (GHR, 10.47), tripeptide-4 (LGD, 3.37), tripedie-5 (KVK, 9.37), tripeptide-6 (GXP, 5.98), tripeptide-8 (HFR, 10.47), tripeptide-10 (KDI, 6.34), RGD peptide (RGD, 6.5), AHK peptide (AHK, 9.07), tripeptide-29 (GPX, 5.98), tripeptide-54 (FTY, 5.98), biotinoyl tripeptide-1 (GHK, 9.07), thioctoyl tripeptide-1 (GHK, 9.07), tripeptide (RFK, 10.61), HGG peptide (HGG, 7.37), RKR peptide (RKRM; SEQ ID NO: 1, 11.84), tetrapeptide-1 (LPTV; SEQ ID NO: 2, 5.98), tetrapeptide-2 (KDVY, 6.34; SEQ ID NO: 3), tetrapeptide-3 (KGHK, 9.37; SEQ ID NO: 4), tetrapeptide-5 (AHSH; SEQ ID NO: 5, 7.52), tetrapeptide-7 (GQPR; SEQ ID NO: 6, 10.47), tetrapeptide-9(QDVH; SEQ ID NO: 7, 4.78), tetrapeptide-11 (PPYL; SEQ ID NO: 8, 5.98), tetrapeptide-15 (YPFF, 5.98; SEQ ID NO: 9), tetrapeptide-21

(GEKG, 6.6; SEQ ID NO: 10), tetrapeptide-26(ELPS; SEQ ID NO: 11, 3.64), acetyl tetrapeptide-2 (KDVY; SEQ ID NO: 12, 6.34), acetyl tetrapeptide-3 (KGHK; SEQ ID NO: 13, 9.37), acetyl tetrapeptide-5 (AHSH; SEQ ID NO: 14, 7.52), acetyl tetrapeptide-9 (QDVH; SEQ ID NO: 15, 4.78), acetyl tetrapeptide-11 (PPYL; SEQ ID NO: 16, 5.98), acetyl tetrapeptide-15 (YPFF; SEQ ID NO: 17, 5.98), pentapeptide-3 (GPRPA, 10.47; SEQ ID NO: 18), pentapeptide-4 (KTTKS; SEQ ID NO: 19, 9.37), pentapeptide-17 (KLAKK, 9.54; SEQ ID NO: 20), pentapeptide-18 (YAGFL; SEQ ID NO: 21, 5.98), thioctoyl pentapeptide-4 (KTTKS; SEQ ID NO: 22, 9.37), hexapeptide-e1 (ARHLFW; SEQ ID NO: 23, 10.47), hexapeptide-2 (FWFKPV; SEQ ID NO: 24, 9.07), hexapeptide-3 (EEMQRR; SEQ ID NO: 25, 6.91), hexapeptide-4 (FGHXAF; SEQ ID NO: 26, 7.37), hexapeptide-5 (FGVXAF; SEQ ID NO: 27, 5.98), hexapeptide-6 (VEPIPY; SEQ ID NO: 28, 6.9 1), hexapeptide-9 (GPQGPQ; SEQ ID NO: 29, 5.98), hexapeptide-11 (FVAPFP; SEQ ID NO: 30, 5.98), hexapeptide-12 (VGVAPG; SEQ ID NO: 31, 5.98), acetyl hexapeptide-3 (EEMQRR; SEQ ID NO: 32, 6.91), acetyl hexapeptide-8 (EEMQRR; SEQ ID NO: 33, 6.91), heptapeptide-6 (HWAWFK; SEQ ID NO: 34, 9.07), cysteine peptide (RFAACAA; SEQ ID NO: 35, 8.33), palmitoyl dipeptide-6 (KV, 9.07), palmitoyl dipeptide-7 (KT, 9.07), azelaoyl tripeptide-1 (GHK, 9.07), palmitoyl-tripeptide-3 (GHR, 10.47), palmitoyl tripeptide-5 (KVK, 9.37), palmitoyl tripeptide-1 (GHK, 9.07), palmitoyl tripeptide-5 (KVK, 9.37), palmitoyl tripeptide (RFK, 10.61), myristoyl tripeptide-1 (GHK, 9.07), palmitoyl tripeptide-4 (LGD, 3.37), palmitoyl tripeptide-8 (HFR, 10.47), palmitoyl tetrapeptide-7 (GQPR; SEQ ID NO: 36, 10.47), myristoyl pentapeptide-17 (KLAKK; SEQ ID NO: 37, 9.54), palmitoyl pentapeptide-4 (KTTKS; SEQ ID NO: 38, 9.37), palmitoyl pentaeptide-17 (KLAKK; SEQ ID NO: 39, 9.54), myristoyl hexapeptide-12 (VGVAPG; SEQ ID NO: 40, 5.98), and palmitoyl hexapeptide-12 (VGVAPG; SEQ ID NO: 40, 5.98), and may have a size of 2mer or more and 10 mer or less. When the peptide in the above range is used, it is preferable in that it can exhibit excellent amorphousness.

The present invention is characterized by comprising a wide range of X-ray diffraction patterns formed in the range of 15 to 25°. The peak formed in the above range may have a single-valued peak widely formed, but a pattern including one or more small peaks may be formed in the above range. When the peak pattern as described above is included, it may mean that amorphousness is high. In the case of a metal compound having high crystallinity, a peak having a narrow and high shape is formed at a specific value, whereas a peak having a shape formed in a wide range may mean having a high ratio of amorphousness in one unit cell. Specifically, as can be seen from the TEM images of FIGS. 26 to 29, the present invention is a metal compound in which amorphous form and crystalline form are mixed, and thus one or more small peaks exhibiting the crystalline form may be included within a wide peak range exhibiting amorphousness formed between 15 to 25°. That is, in addition to the peak of amorphous form, a peak exhibiting crystallinity may be included in the peak of amorphous form.

In addition, in the metal phase transformation compound of the present invention, the powder X-ray diffraction pattern may include peak values of diffraction angle (2θ) =19±6°, 33±5° and 59±5° and may include one or more peaks within the peak formed in the range of 15 to 25°.

In addition, in the metal phase transformation compound of the present invention, 20% by weight or more peptide may be contained within one unit cell, more preferably 30% by weight or more peptide, still more preferably 40% by weight or more peptide, still yet more preferably 50% by weight or more peptide may be contained therein.

In addition, the metal phase transformation compound of the present invention may preferably contain 20 to 80% by weight peptide within one unit cell and 10 to 35% by weight metal, more preferably 30 to 80% by weight peptide within one unit cell and 10 to 35% by weight metal, still more preferably 40% to 80% by weight peptide within one unit cell and 10 to 35% by weight metal.

Therefore, the present invention can provide an external composition for skin comprising the metal phase transformation compound described above. The external composition for skin is expected to be used as a raw material for cosmetics, quasi-drugs, and hygiene products having improved functionality through improvement of skin transfer efficiency of functional peptides. In addition, the external composition for skin may be prepared in a variety of formulations, and may be prepared in formulations, for example, a cream, gel, ointment, lotion, serum, etc.

In case of a method for preparing the metal phase transformation compound of the present invention can be used without limitation if it is a conventional method for preparing the metal compound, but it may be preferable in that amorphousness in the metal compound can be improved in a case of being prepared by including a step of separately preparing a metal solution, a peptide solution, and a hydroxide solution, respectively, and a step of mixing the separately prepared solution.

In addition, in the method for preparing the metal phase transformation compound, a ratio of ethanol and water in the total solution and solvent used in terms of the total solution and solvent used in the entire preparation method may be used in a range of 10:90 to 90:10 of ethanol:water in volume ratio. In particular, it may be more preferable that the ethanol used in the present invention has a purity of 95% or more. When the ratio of water and ethanol in the solution and solvent satisfies the above range, it is preferable in that amorphousness in the metal compound can be enhanced.

Method for Preparing Metal Phase Transformation Compound

In the present invention, during the synthesis of the metal phase transformation compound, all processes are performed at room temperature (20° C.) and under a nitrogen atmosphere. In addition, 95% ethanol and tertiary distilled water were used, and PEP (peptide) with a purity of 95% or more (moisture content of 5% or less) was used. The aqueous NaOH solution was 3.2M and was prepared with tertiary distilled water. The method for preparing the metal phase transformation compound is performed as follows in the sequence of synthesis-washing-drying. After feeding the weight equivalent to 0.4 equiv to 0.13 equiv of PEP to tank 1, add tertiary distilled water and a co-solvent containing 30% or more of ethanol (95%<) compared to ethanol into tank 1, and the mixture is stirred. After feeding the weight equivalent to 1 equiv of ZnO to tank 2, the conc. HCl solution in auxiliary tank 1 is slowly added dropwise to the main tank, titrated to a pH of 0.5 to 1, and dissolved while stirring at 700 rpm for about 30 minutes under a nitrogen atmosphere.

Thereafter, a 3.2M NaOH solution in tank 3 is prepared, and after adding the solutions in tanks 1, 2, and 3 to the main tank, titrated so that the pH of the main tank is maintained at 6.5 to 7.5, a precipitation reaction is induced in the main tank while stirring for 3 hours, and the pH is maintained between 6.5 and 7.5.

The following step is the washing process of the precipitate, and impurities are removed using a centrifuge to remove unreacted salts and ionic substances from the solution. Centrifugation is performed 4 times at 9000 rpm for 5 minutes each to separate the precipitate and solution, and the sequence is as follows. The synthesized precipitate solution was centrifuged at 9000 rpm for 5 minutes. After separating the solution and the precipitate, the precipitate is evenly diluted in a 1:1 ratio of ethanol and tertiary distilled water, and was centrifuged at 9000 rpm for 5 minutes. This process is repeated 4 times. In the last centrifugal washing, it is diluted with only distilled water, and then centrifuged at 9000 rpm for 10 minutes to obtain a precipitate.

EXAMPLE: METAL PHASE TRANSFORMATION COMPOUND OF EXAMPLES 1 TO 8

Synthesis of Example 1

As the basic conditions of the experiment, all processes are performed at room temperature (20° C.) and under a nitrogen atmosphere. In addition, 95% ethanol and tertiary distilled water were used, and PEP with a purity of 95% or more (moisture content of 5% or less) was used. NaOH aqueous solution is 3.2M and is prepared with tertiary distilled water.

The experiment is performed as follows in the sequence of synthesis-washing-drying. After feeding 2.845 g of palmitoly-GHK and 30 ml of ethanol to tank 1, the mixture is stirred. After feeding 1 g of ZnO, 5 ml of tertiary distilled water, and 15 ml of ethanol to tank 2, the conc. HCl solution in auxiliary tank 1 is added dropwise to the main tank, titrated to a pH of 1 (0.5<) or less, and is dissolved while stirring the mixture at 500 rpm for about 30 minutes under a nitrogen atmosphere.

Thereafter, a 3.2M NaOH solution in tank 3 is prepared, and after adding the solutions in tanks 1, 2, and 3 to the main tank, titrated so that the pH of the main tank is maintained at 6.5 to 7.5, a precipitation reaction is induced in main tank while stirring the mixture at 700 rpm for 3 hours, and the pH is maintained between 6.5 and 7.5 (total amount of solvent to be added is maintained at 30% or more compared to ethanol).

The following step is the washing process of the precipitate, and impurities are removed using a centrifuge to remove unreacted salts and ionic substances from the solution. Centrifugation is performed 4 times at 9000 rpm for 5 minutes each to separate the precipitate and solution, and the sequence is as follows. The synthesized precipitate solution was centrifuged at 9000 rpm for 5 minutes. After separating the solution and the precipitate, the precipitate is evenly diluted in a 1:1 ratio of ethanol and tertiary distilled water, and was centrifuged at 9000 rpm for 5 minutes. This process is repeated 4 times. In the last centrifugal washing, it is diluted with only distilled water, and then centrifuged at 9000 rpm for 10 minutes to obtain a precipitate. The compounds used in the specific synthesis and the synthesis results are listed in Table 1 below.

Figure 3:
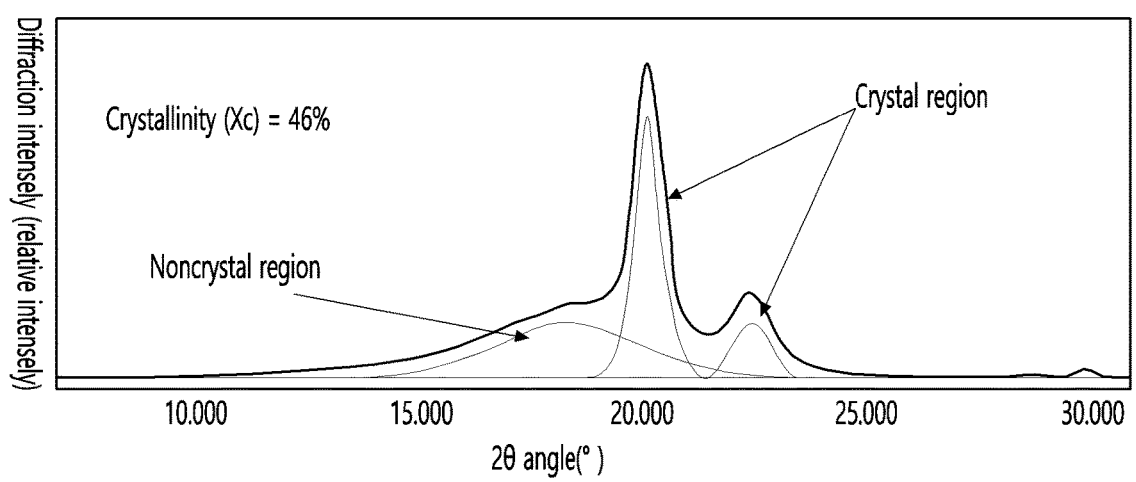
FIG. 3 is a graph of the crystallinity related to the crystalline form ratio.
Figure 4:
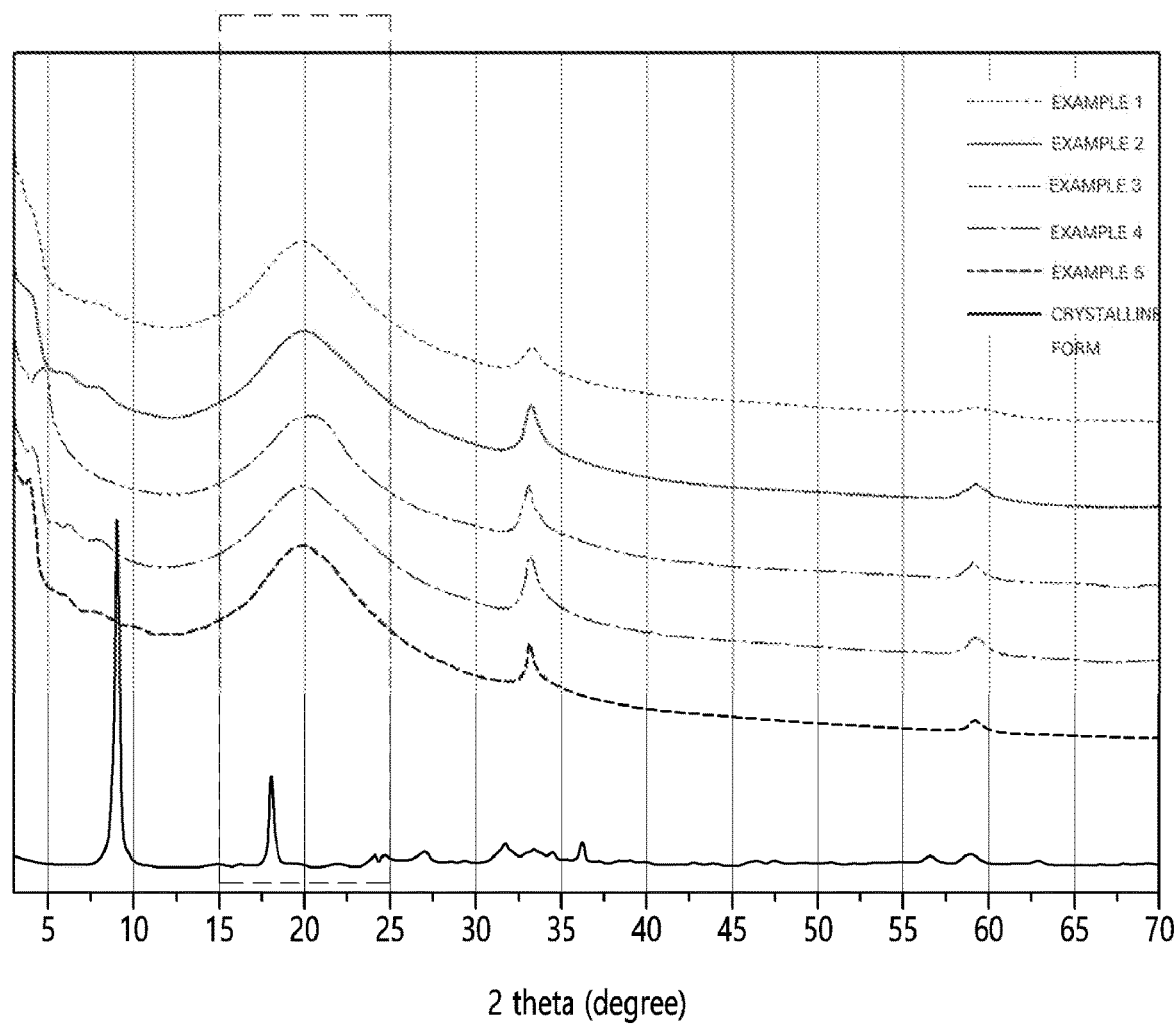
FIG. 4 is a diagram comparing XRD graphs of Examples 1 to 5 with an XRD graph of crystalline ZBS that does not contain a peptide of Reference Example.
Figure 5:
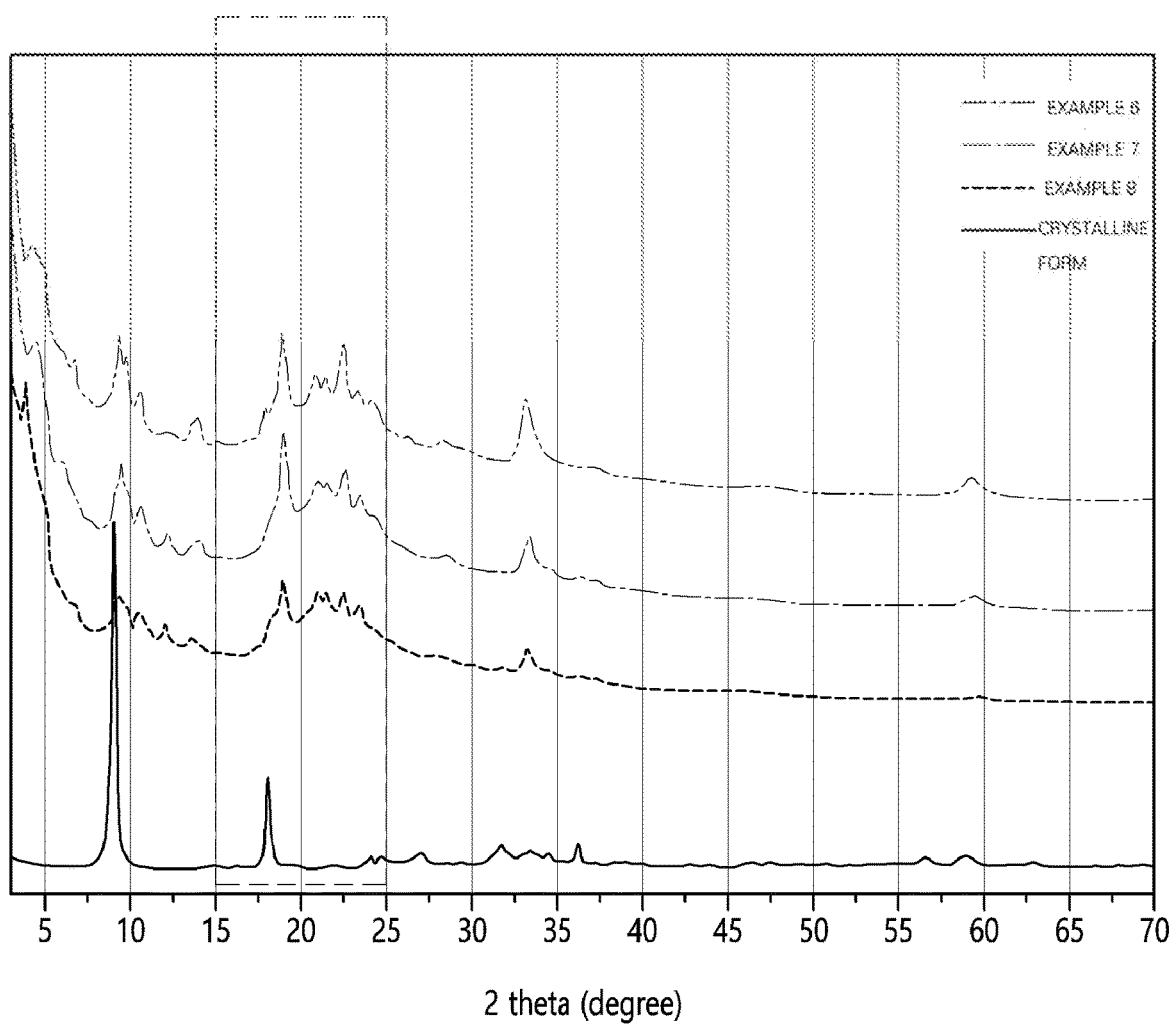
FIG. 5 is a diagram comparing the XRD graphs of Examples 6 to 8 with the XRD graph of crystalline ZBS that does not contain the peptide of Reference Example.

The crystallinity is determined by the following formula, and a graph related to the crystallinity is illustrated in FIG. 3.

$$\text{Degree of crystallinity}(\%) = \frac{\text{crystal-derived scattering intensity}}{\text{crystal-derived scattering intensity} + \text{Noncrystal-derived scattering intensity}} \quad [\text{Formula 1}]$$

Examples 2 to 5

In the same manner as in the synthesis method for Example 1, the metal phase transformation compounds of Examples 2 to 5 were synthesized as described in Table 1. The synthesis results are also listed in Table 1 below.

TABLE 1

| step | sort | material | Example 1 usage (g) | mole | Example 2 usage (g) | mole | Example 3 usage (g) | mole | Example 4 usage (g) | mole | Example 5 usage (g) | mole |
|---|---|---|---|---|---|---|---|---|---|---|---|---|
| $1^{st}$ | A | PEP 1 | 2.845 | 0.0049152 | 2.845 | 0.0049152 | 2.845 | 0.0049152 | 2.845 | 0.0049152 | 2.845 | 0.0049152 |
| | solvent | EtOH | 30 | | 27.5 | | 15 | | 10 | | 10 | |
| | | $H_2O$ | 0 | | 0 | | 0 | | 0 | | 0 | |
| | | Sub-total | 30 | | 27.5 | | 15 | | 10 | | 10 | |
| | B | ZnO | 1 | 0.12288 | 1 | 0.12288 | 1 | 0.12288 | 1 | 0.12288 | 1 | 0.12288 |
| | | Conc. HCl (pH) | 0.16 | | 0.16 | | 0.16 | | 0.16 | | 0.16 | |
| | solvent | EtOH | 15 | | 10 | | 10 | | 2.5 | | 0 | |
| | | $H_2O$ | 5 | | 12.5 | | 25 | | 37.5 | | 40 | |
| | | Sub-total | 25 | | 22.5 | | 35 | | 40 | | 40 | |
| | C | | 6.12 | | 6.12 | | 6.12 | | 6.12 | | 6.12 | |
| $2^{nd}$ | A + B + C | Stirring | | | | | | | | | | |
| $3^{rd}$ result | | Washing step | | | | | | | | | | |
| | | yield (%) | 3.38 | | 3.08 | | 2.86 | | 2.1 | | 2.1 | |
| | | yield (%) | 84.73 | | 85.22 | | 84.97 | | 83.25 | | 83.25 | |
| | | Color | White off | | White off | | White off | | White off | | White off | |
| | Content % | Zn (%) | 19.950 | | 20.080 | | 24.090 | | 18.640 | | 18.640 | |
| | | PEP1 | 71.18 | | 72.11 | | 68.51 | | 76.26 | | 76.26 | |
| | | Crystallinity (%) | 2.74 | | 2.74 | | 2.71 | | 2.77 | | 4.7 | |

(*PEP1: palmitoyl-GHK)

In the case of the conventional crystalline metal hydroxide complex, palmitoyl-GHK peptide could be contained up to 40%. However, looking at Examples 1 to 5, it was confirmed that the metal phase transformation compound contained a peptide content of 60% or more, and the characteristics of the active ingredient content were remarkably improved. In addition, for this purpose, the co Amorphous-Crystalline was artificially induced by adjusting the ratio of ethanol during the experiment, and the result can be seen through the XRD pattern.

Examples 6 to 8

Except for the contents and types of peptides listed in Table 2, the metal phase transformation compounds of Examples 6 to 8 were synthesized in the same manner as in the synthesis method for Example 1. The synthesis results are also listed in Table 2 below.

TABLE 2

| step | sort | material | Example 6 usage (g) | mole | Example 7 usage (g) | mole | Example 8 usage (g) | mole |
|---|---|---|---|---|---|---|---|---|
| $1^{st}$ | A | PEP 2 | 0.949 | 0.001832 | 0.949 | 0.001832 | 0.949 | 0.001832 |
| | solvent | EtOH | 25 | | 15 | | 10 | |

TABLE 2-continued

| step | sort | material | | Example 6 usage (g) | Example 6 mole | Example 7 usage (g) | Example 7 mole | Example 8 usage (g) | Example 8 mole |
|---|---|---|---|---|---|---|---|---|---|
| | | $H_2O$ | | 0 | | 0 | | 0 | |
| | | Subtotal | | 25 | | 15 | | 10 | |
| | B | $Zn(NaOH)_2 \cdot 6H_2O$ | | 0.88 | 0.0029581 | 0.88 | 0.0029581 | 0.88 | 0.0029581 |
| | | solvent | EtOH | 25 | | 10 | | 0 | |
| | | | $H_2O$ | 0 | | 25 | | 40 | |
| | | Subtotal | | 25 | | 35 | | 40 | |
| | C | 3.2M NaOH | | 1.7 | | 1.7 | | 1.7 | |
| $2^{nd}$ | A + B + C | Stirring | | | | | | | |
| $3^{rd}$ | | Washing step | | | | | | | |
| result | | yield (%) | | 0.97 | | 0.97 | | 0.95 | |
| | | yield (%) | | 69.59 | | 68.59 | | 67.19 | |
| | | Color | | White off | | White off | | White off | |
| | Content % | Zn (%) | | 16.590 | | 20.080 | | 24.090 | |
| | | PEP2 | | 74.37 | | 77.82 | | 78.14 | |
| | | Crystallinity (%) | | 10.7 | | 10.6 | | 6.8 | |

(*PEP2: palmitoyl-pentapeptide4)

In the case of the conventional crystalline metal hydroxide complex, palmitoyl-pentapeptide4 peptide could be contained up 20%. However, looking at Examples 6 to 8, it was confirmed that the metal phase transformation compound contained a peptide content of 60% or more, and the characteristics of the active ingredient content were remarkably improved. In addition, for this purpose, the co Amorphous-Crystalline was artificially induced by adjusting the ratio of ethanol during the experiment, and the result can be seen through the XRD pattern.

Reference Example: Method for Preparing Zinc Layered Hydroxide

After dissolving 5 g of $Zn(NO_3)_2 \cdot 6H_2O$ in tertiary distilled water from which carbonate ions ($CO_3^{2-}$) have been removed, the pH was titrated to about 6 to 7 using 0.2M NaOH to obtain a zinc basic salt precipitate. The titrated solution was separated by a centrifuge and unreacted salt was removed through a washing process to prepare 2.6 g (yield 70%) of white powder.

Comparative Example: Method for Preparing Crystalline Metal Hydroxide Containing Peptide As the basic conditions of the experiment, all processes are performed at room temperature (20° C.) and under a nitrogen atmosphere. In addition, 95% ethanol and tertiary distilled water were used, and a peptide with a purity of 95% or higher (moisture content less than 5%) was used. NaOH aqueous solution is 3.2M and is prepared with tertiary distilled water.

The peptide used in the present invention is palmitoyl GHK.

The experiment is performed in the sequence of synthesis-washing-drying as follows.

After feeding 3 g of $Zn(NO_3)_2$ $6H_2O$, 25 ml of ethanol, and 25 ml of tertiary distilled water to the main tank, the mixture is dissolved while stirring the mixture at 700 rpm for about 30 minutes. After dissolving 0.58 g of peptide and 20 ml of ethanol, and 10 ml of tertiary distilled water in the auxiliary tank 1, the mixture was added to the main tank (total amount of solvent was 25 volume compared to Zn input) and is dissolved while stirred at 300 rpm for 5 minutes. The stirring speed of the main tank is maintained, a 3.2M NaOH solution is added from the auxiliary tank 2 to the main tank, and then is titrated so that the pH of the main tank is maintained between 6.5 and 7.5, and a precipitation reaction is induced in the main tank while stirring for 3 hours, and the pH is maintained between 6.5 and 7.5.

The following step is the washing process of the precipitate, and impurities are removed using a centrifuge to remove unreacted salts and ionic substances from the solution. Centrifugation is performed 3 times at 8000 rpm for 5 minutes each to separate the precipitate and solution, and the sequence is as follows. The synthesized precipitate solution was centrifuged at 8000 rpm for 5 minutes. After separating the solution and the precipitate, the precipitate is evenly diluted in a 1:1 ratio of ethanol and tertiary distilled water, and was centrifuged at 8000 rpm for 5 minutes. This process is repeated 3 times. In the last centrifugal washing, it is diluted with only distilled water, and then centrifuged at 9000 rpm for 10 minutes to obtain a precipitate.

Figure 14:
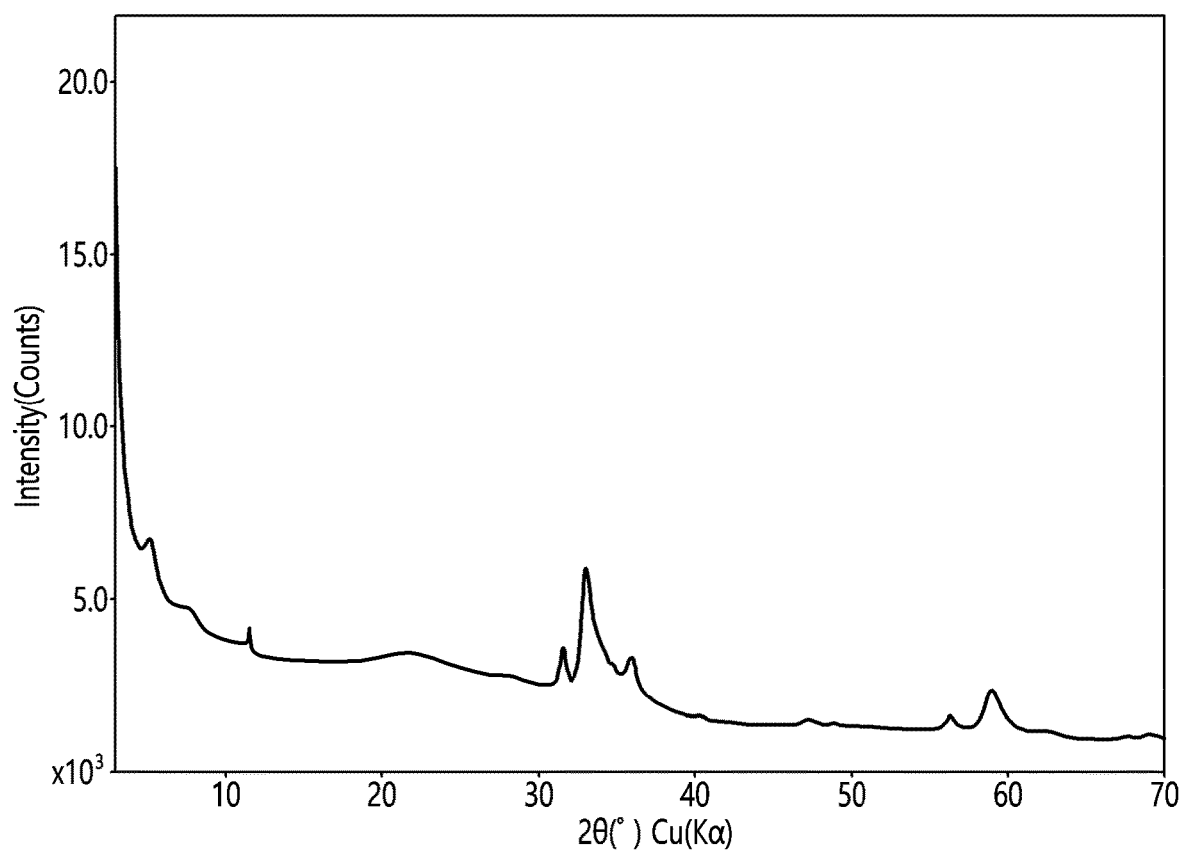
FIG. 14 is an XRD graph of a comparative example.

It was confirmed that the content of the peptide contained within one unit cell of the comparative example was 20%, and the XRD graph thereof is illustrated in FIG. 14.

Experimental Example 1: Measurement of XRD Peak of Metal Compound

Instrument: Powder X-Ray Diffraction (PXRD)

X-ray diffractometer (D/MAXPRINT 2200-Ultima, Rigaku, Japan)

Cu-Kα radiation (λ=1.5418 Å)

Tube voltage 40 kV, current 30 mA

Measurement was performed using D/MAXPRINT 2200-Ultima of Rigaku Corporation (Japan) as the X-ray diffractometer was measured. Cu metal was used as a cathode for generating X-rays, and the measurement range was 2θ=3 to 70° with Kα rays (λ=1.5418 Å), scanning speed: 0.02°/0.2 sec, divergence slit, scattering slit, and receiving slit was measured to be 0.1, 1, and 1 mm, respectively. The tube voltage of 40 kV and a current of 30 mA was applied.

Evaluation Criteria

One-dimensional (1D) electron density with respect to the z-axis is calculated by the following equation.

$$\rho(z) = \sum_{l=0}^{\infty} F_{00l} \cos \frac{2\pi l z}{c}$$ [Equation 1]

The powder obtained through the synthesis was compared and analyzed through the XRD diffraction pattern, and the resultant interlayer distance was calculated through Bragg's equation (Equation 2 below). In the case of the front-most peak, it represents the interlayer distance including the distance between the layer of the synthesized metal compound and the layer in which anions exist, and can be called the main interlayer distance.

$$N\lambda = 2d \sin \theta$$ [Equation 2]

($\lambda$=wavelength of X-ray, d=lattice spacing of crystal, $\theta$=angle of incidence)

The measured XRD patterns are illustrated in FIGS. 4 to 10.

When examining FIGS. 4 to 10, it can be seen that wide peaks are formed between 15 to 25°. That is, it can be confirmed that the co Amorphous-Crystalline in each unit cell is artificially induced in the metal phase transformation compound of the present invention, which can be confirmed through the XRD pattern.

Figure 6:
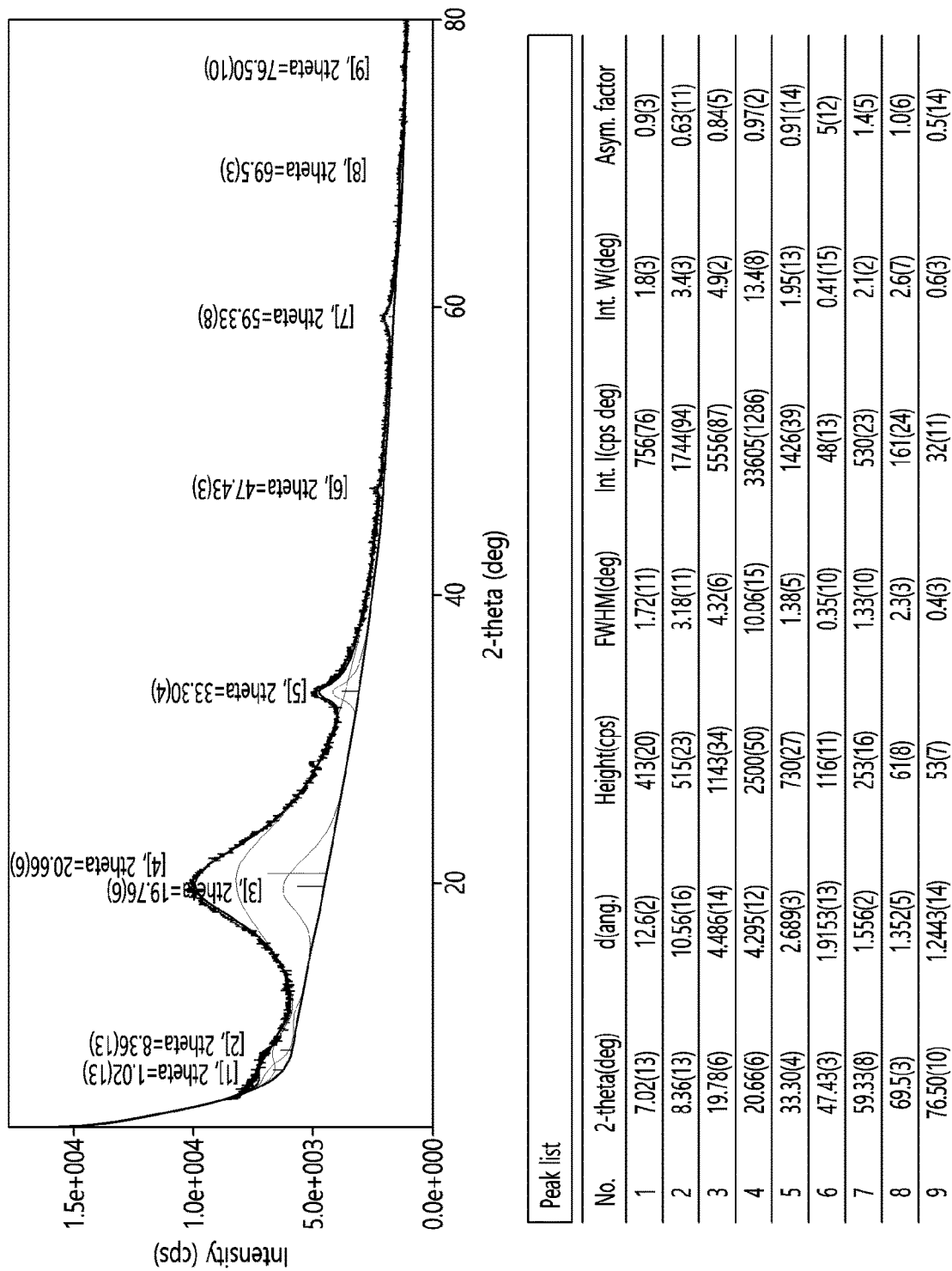
FIG. 6 is the XRD graph of Example 1.

Specifically, in the powder X-ray diffraction pattern of FIG. 6, the diffraction angle (2θ) may include peak values of 7.02±1°, 8.36±1°, 19.78±6°, 20.66±1°, 33.3±5°, 47.43±1°, 59.33±5°, 69.5±1°, and 76.5±1°, and more specifically, has peaks of 7.02±1°, 8.36±1°, 19.78±6°, 20.66±1°, 33.3±5°, 47.43±1°, 59.33±5°, 69.5±1°, and 76.5±1°, and peaks in a wide range are formed in the range of 15 to 25°.

Figure 7:
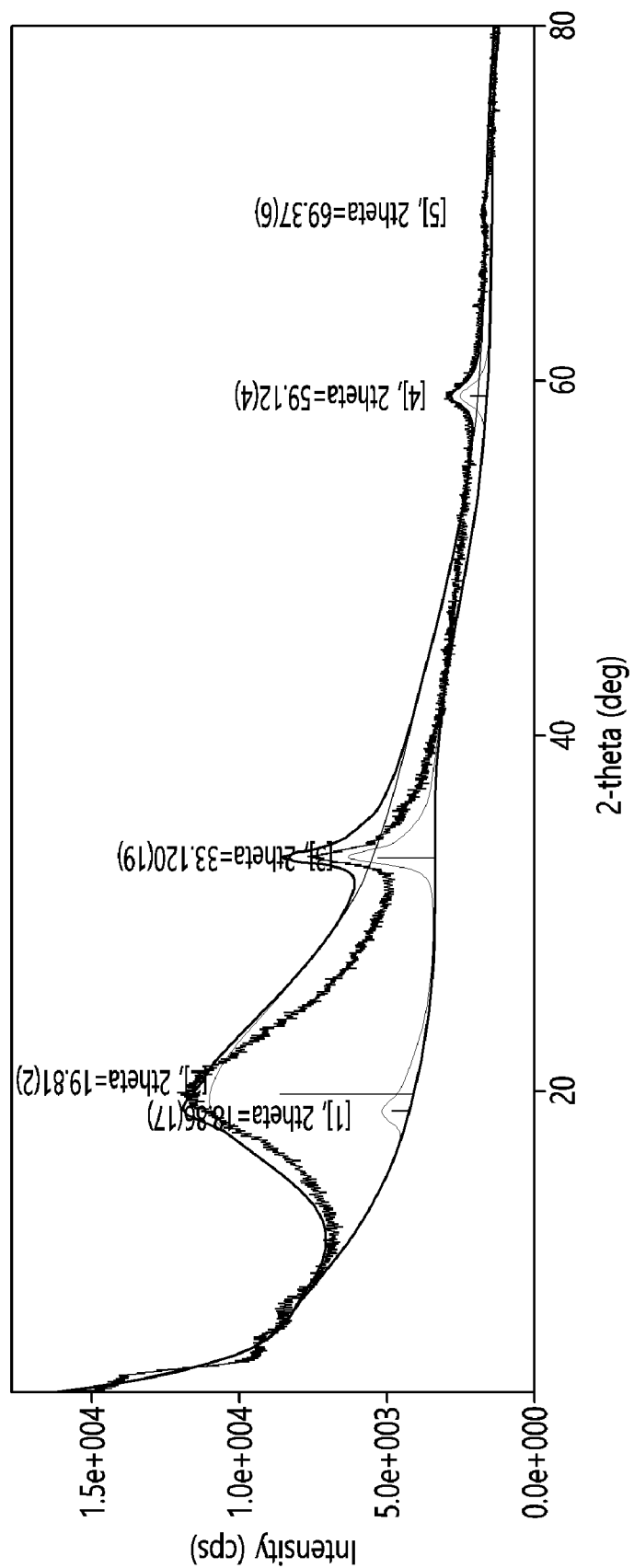
FIG. 7 is the XRD graph of Example 2.

Specifically, in the powder X-ray diffraction pattern of FIG. 7, the diffraction angle (2θ) may include peak values of 18.86±1°, 19.81±6°, 33.3±5°, 59.12±5°, and 69.37±1°, and more specifically, has peaks of 18.86±1°, 19.81±1°, 33.3±1°, 59.12±1°, and 69.37±1°, and peaks in a wide range are formed in the range of 15 to 25°.

Figure 8:
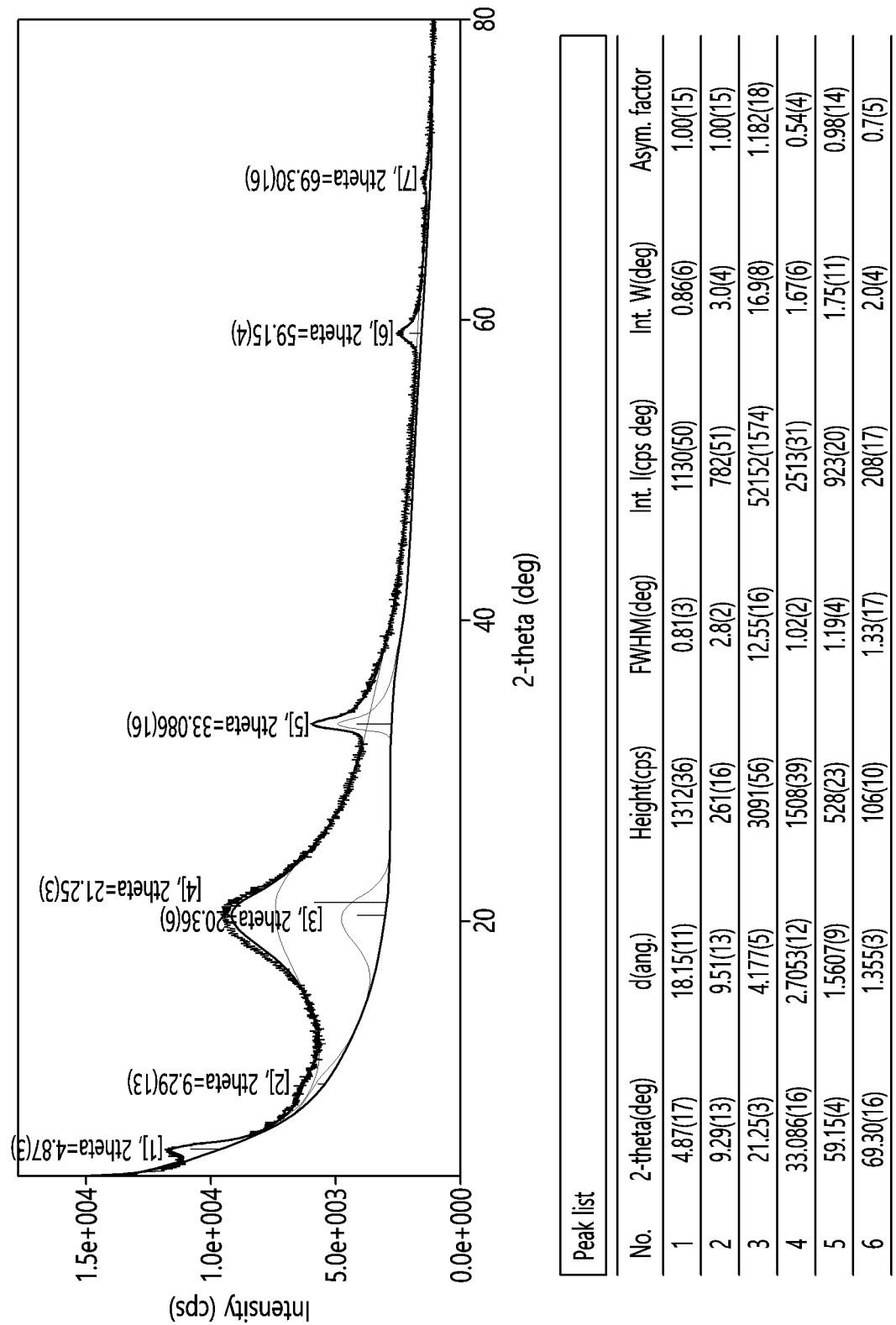
FIG. 8 is the XRD graph of Example 3.

Specifically, in the powder X-ray diffraction pattern of FIG. 8, the diffraction angle (2θ) may include peak values of 4.87±1°, 9.29±1°, 21.25±6°, 33.086±5°, 59.15±5°, and 69.30±1°, and more specifically, has peaks of 4.87±1°, 9.29±1°, 21.25±1°, 33.086±1°, 59.15±1°, and 69.30±1°, and peaks in a wide range are formed in the range of 15 to 25°.

Figure 9:
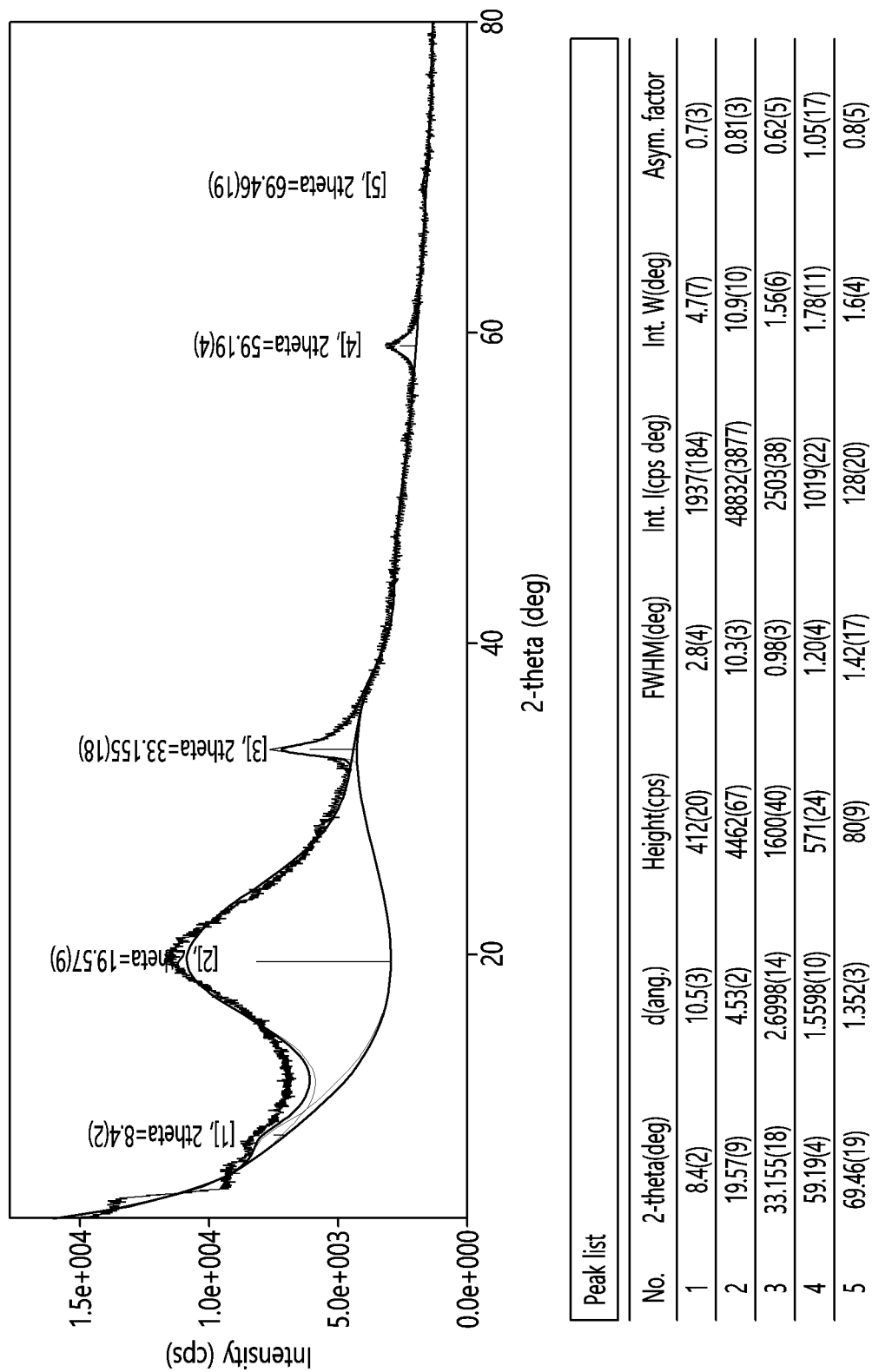
FIG. 9 is the XRD graph of Example 4.

Specifically, in the powder X-ray diffraction pattern of FIG. 9, the diffraction angle (2θ) may include peak values of 8.4±1°, 19.57±6°, 33.155±5°, 59.19±5°, and 69.46±1°, and more specifically, has peaks of 8.4±1°, 19.57±1°, 33.155±1°, 59.19±1°, and 69.46±1°, and peaks in a wide range are formed in the range of 15 to 25°.

Figure 10:
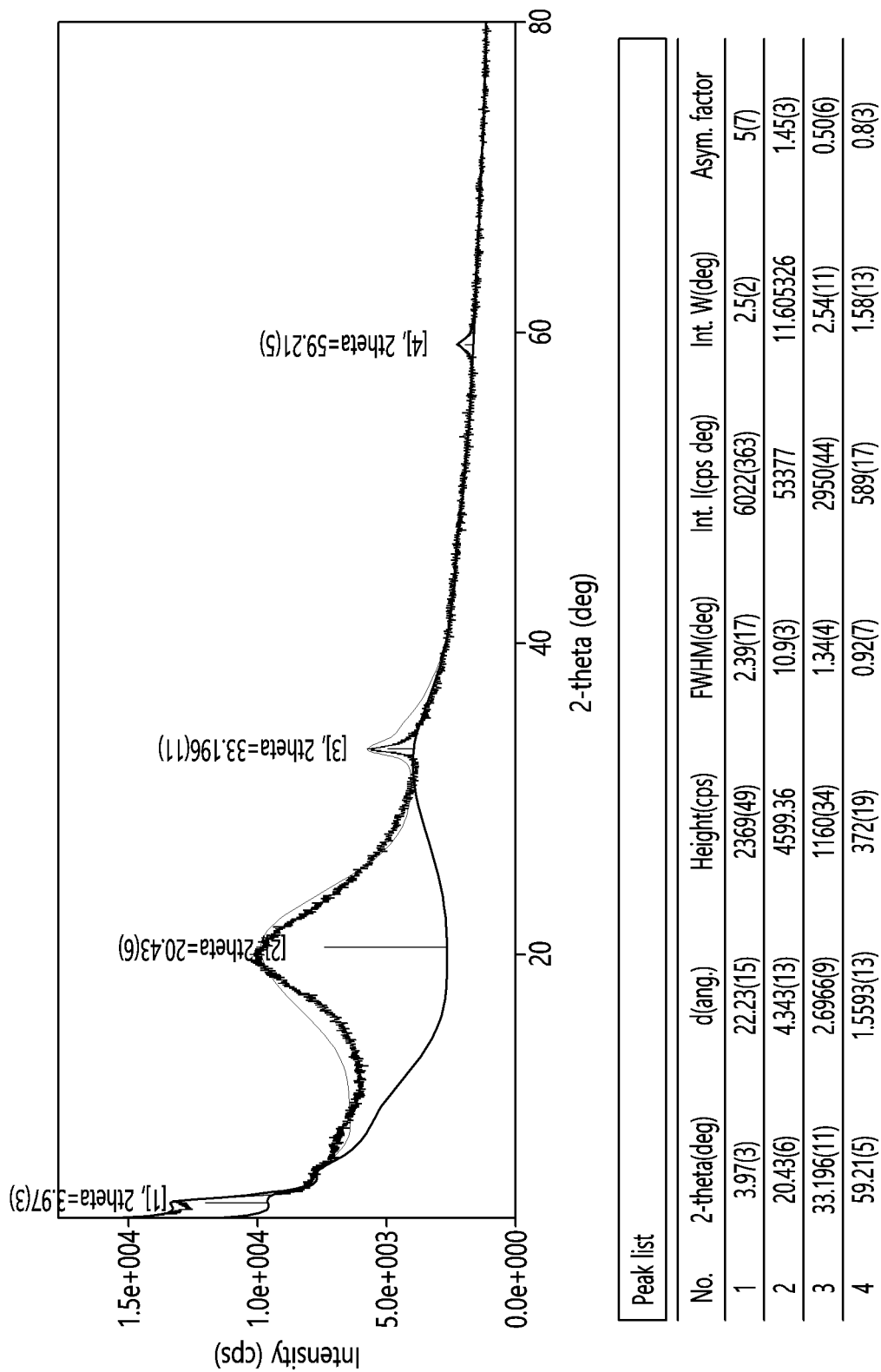
FIG. 10 is the XRD graph of Example 5.
Figure 11:
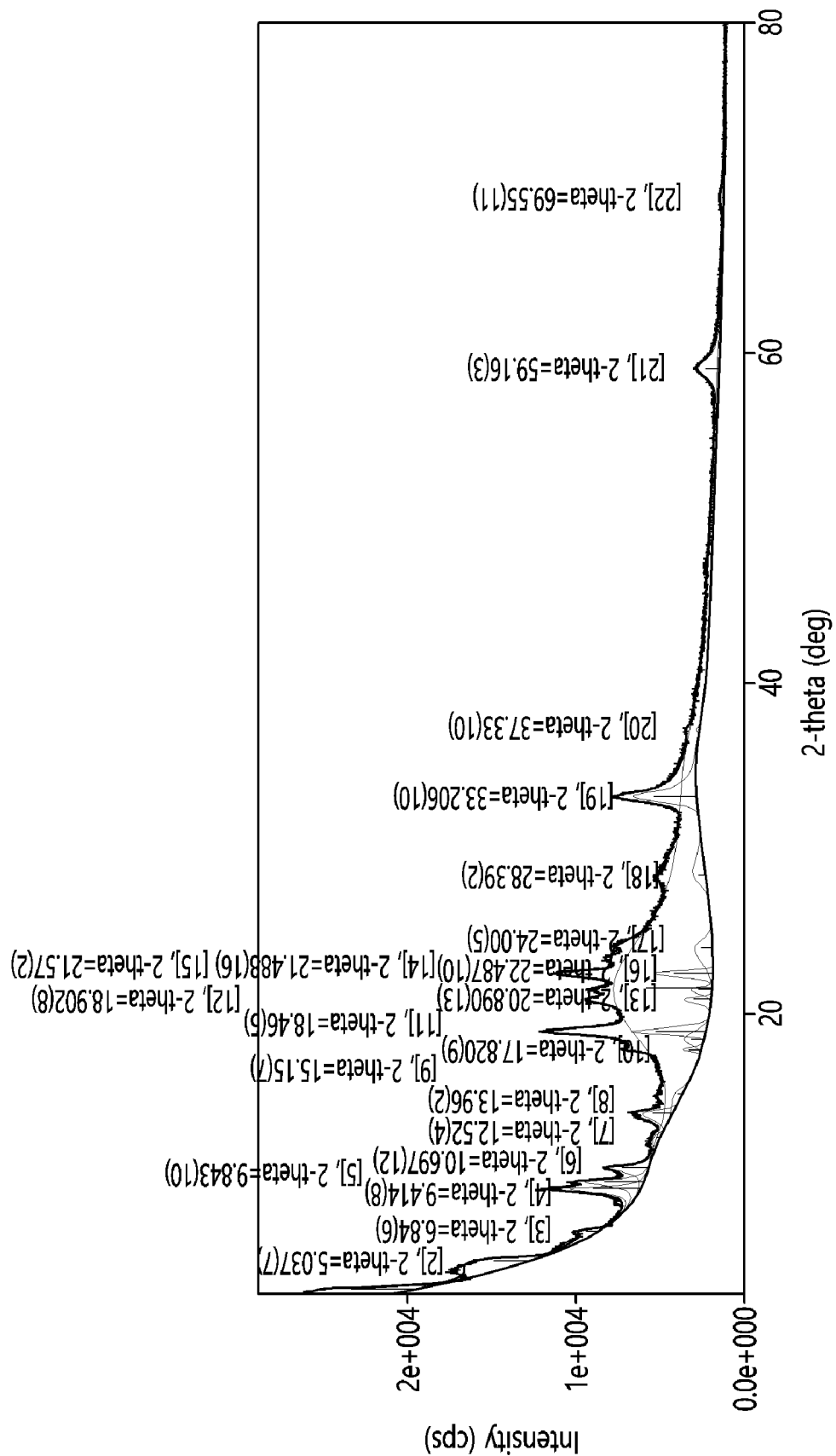
FIG. 11 is the XRD graph of Example 6.
Figure 12:
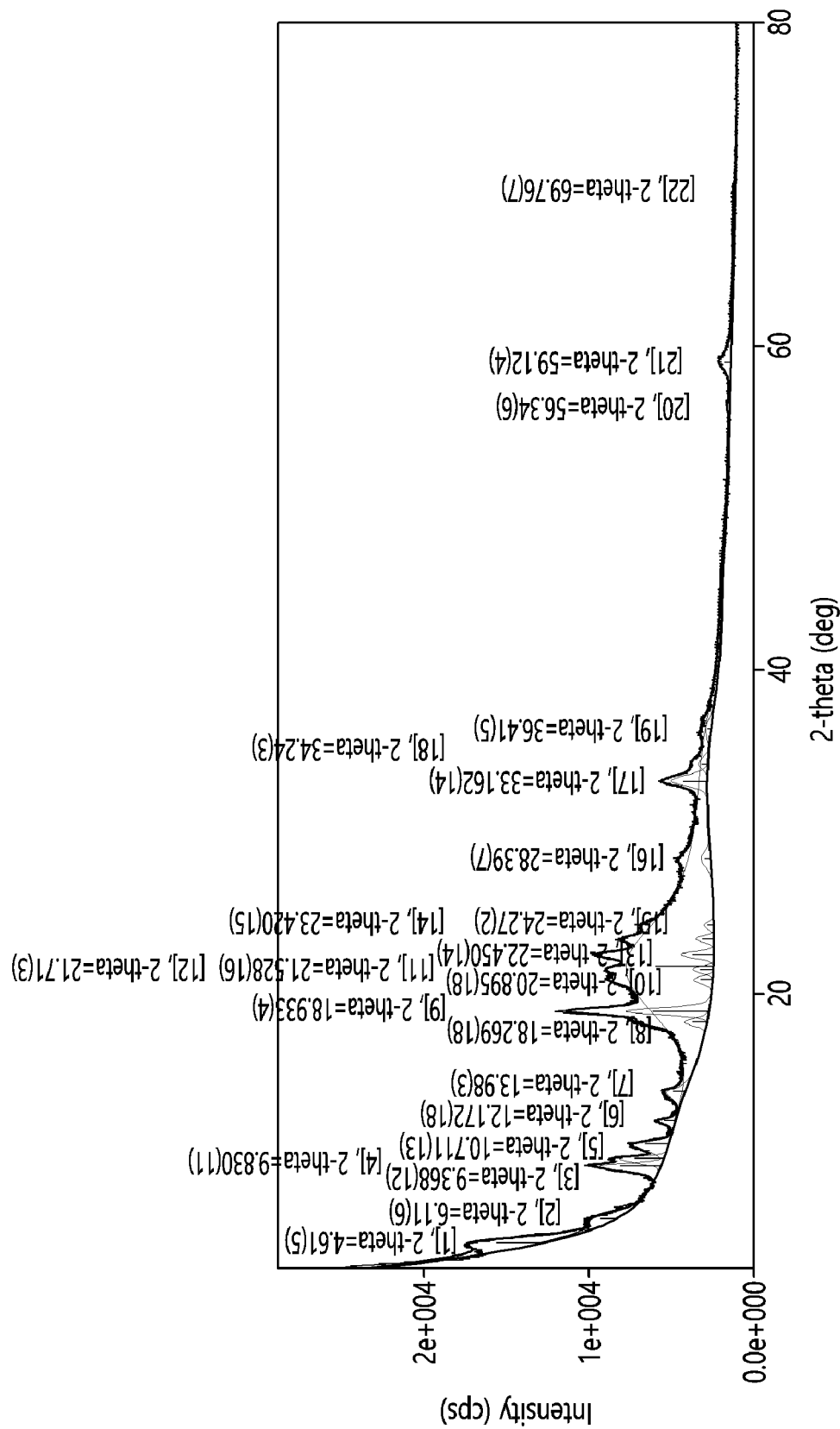
FIG. 12 is the XRD graph of Example 7.
Figure 13:
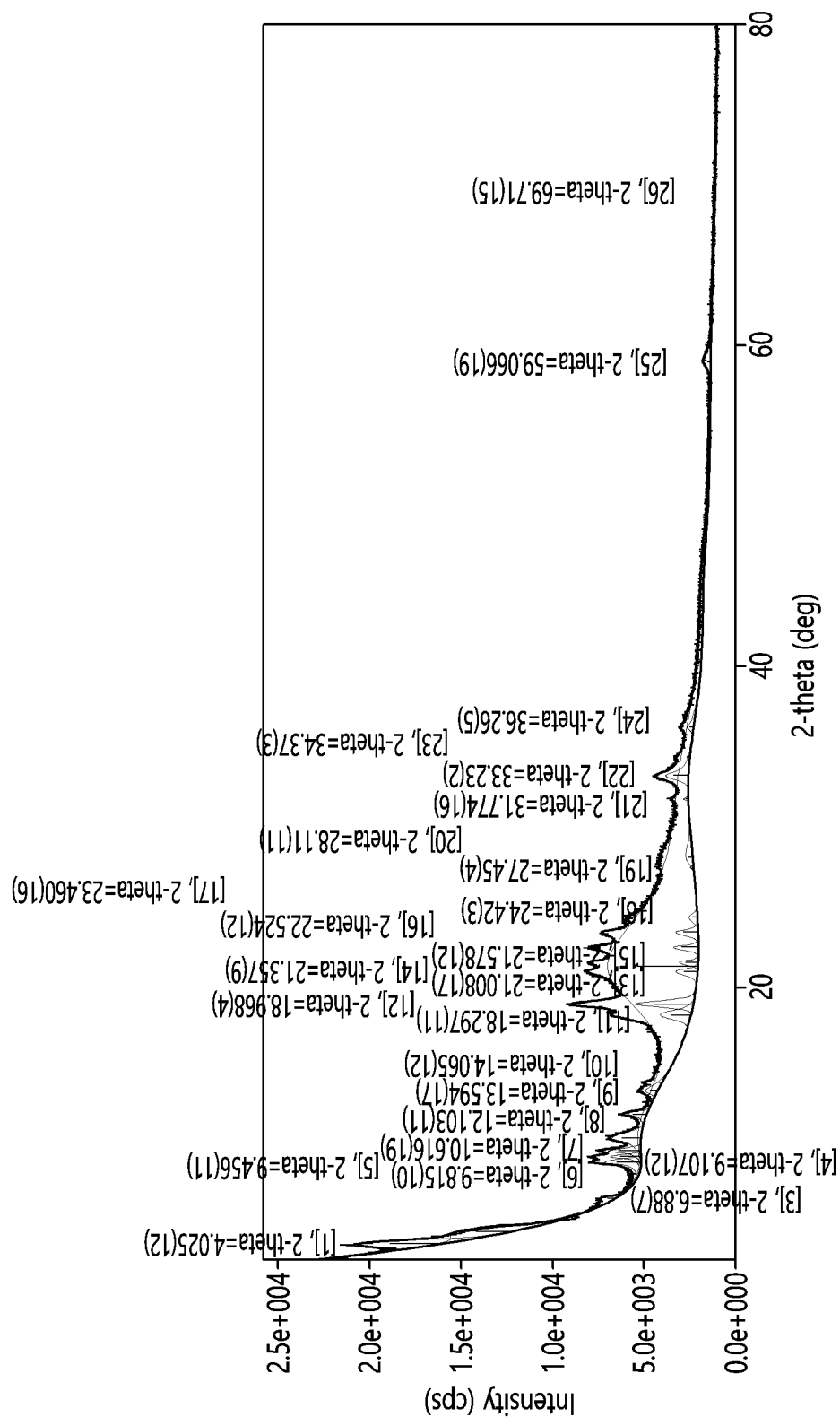
FIG. 13 is the XRD graph of Example 8.

Specifically, in the powder X-ray diffraction pattern of FIG. 10, the diffraction angle (2θ) may include peak values of 3.97±1°, 20.43±6°, 33.196±5°, and 59.21±5°, and more specifically, has peaks of 3.97±1°, 20.43±1°, 33.196±1°, and 59.21±1°, and peaks in a wide range are formed in the range of 15 to 25°.

Experimental Example 2: SEM-EDX (Scanning Electron Microscope-Energy Dispersive X-ray Spectrometer)

The instrument used for Scanning Electron Microscope-Energy Dispersive X-ray Spectrometer (SEM-EDX) was a Field Emission Scanning Electron Microscope (JEOL-7610F-Plus), and the instrument is an analysis device for analyzing and imaging nanostructured materials and device structures.

1. Performance

1) Resolution: 0.8 nm (15 kV)
1.0 nm (1 kV GB mode)
3.0 nm (15 kV, PC 5 nA, WD 8 mm)
2) Magnification: Direct ×25 to ×1,000,000
Display ×75 to 3,000,000
3) Accelerating voltage: 0.01 kV to 30 kV
4) Probe current: A few pA to ≥200 nA

2. Electron Gun

Figure 15:
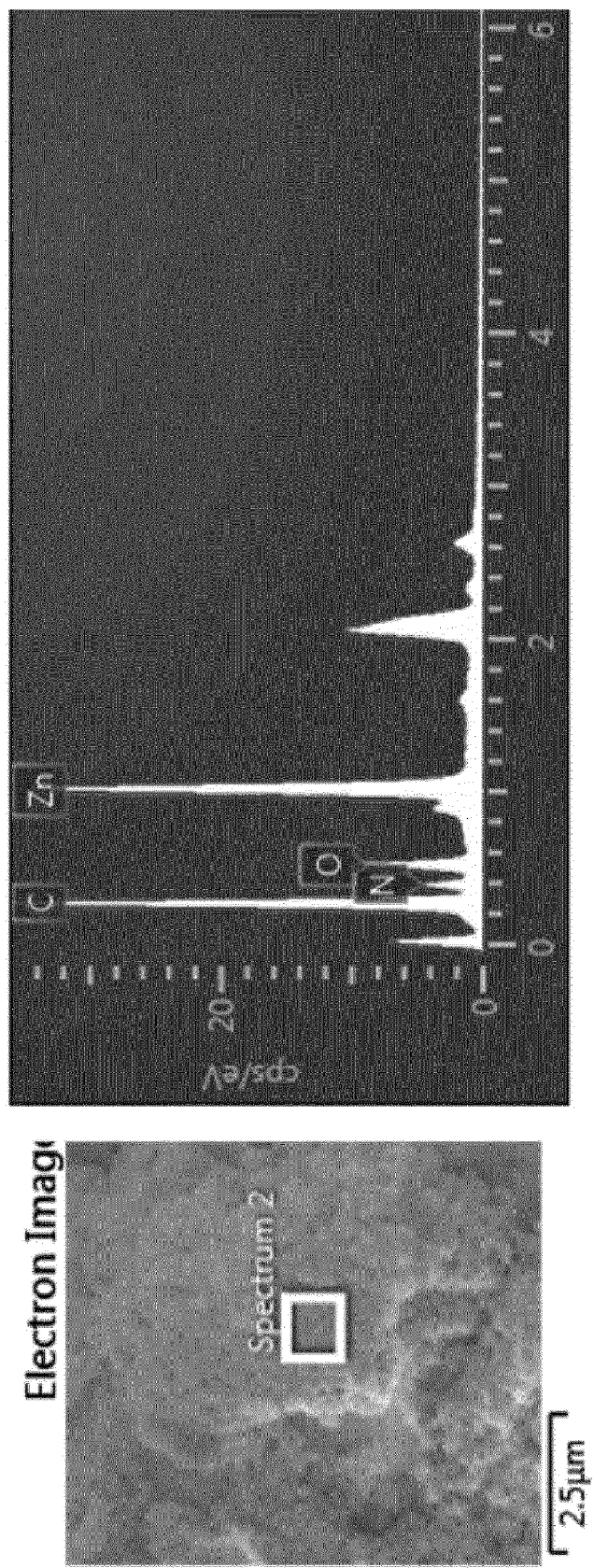
FIG. 15 is a graph illustrating the results of SEM-EDX of Example 3.
Figure 16:
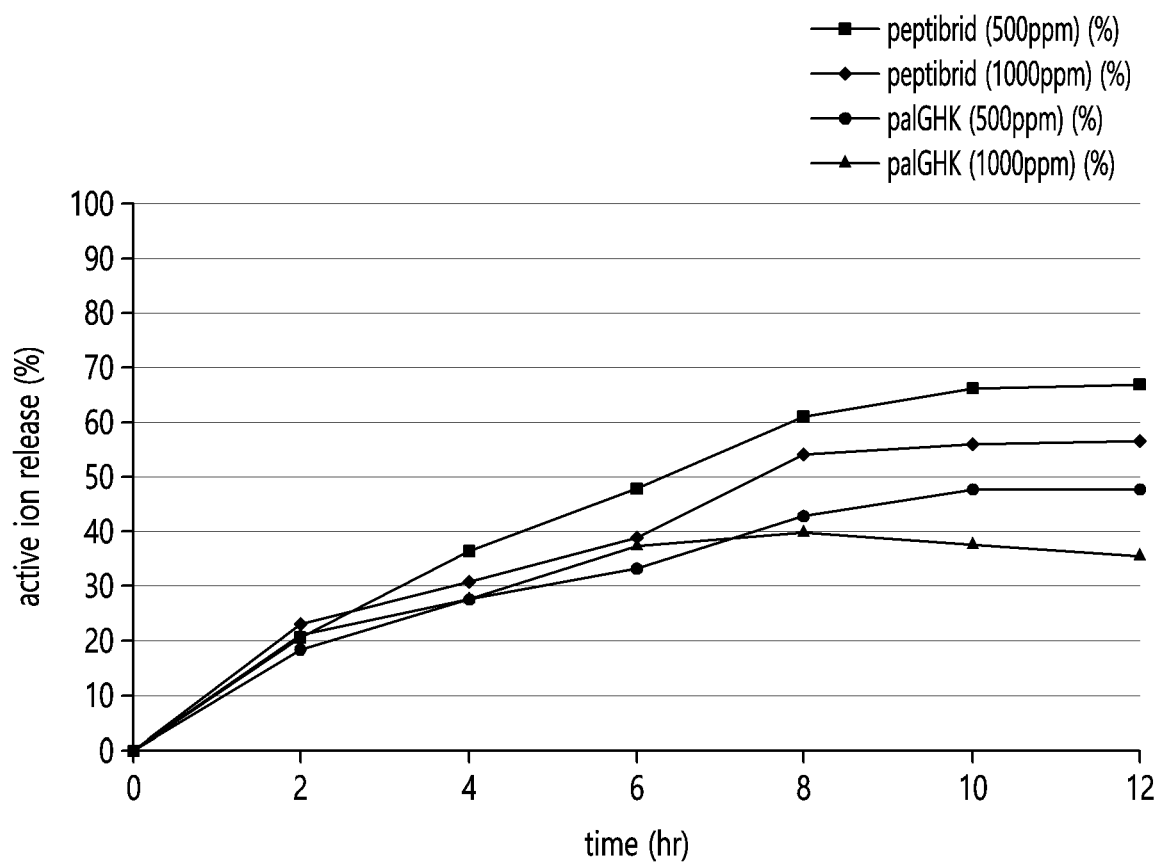
FIG. 16 is a graph of transmittances of Example 3 (peptibrid 500 ppm), Example 3 (peptibrid 1000 ppm), pal-GHK (500 ppm), and pal-GHK (1000 ppm).
Figure 17:
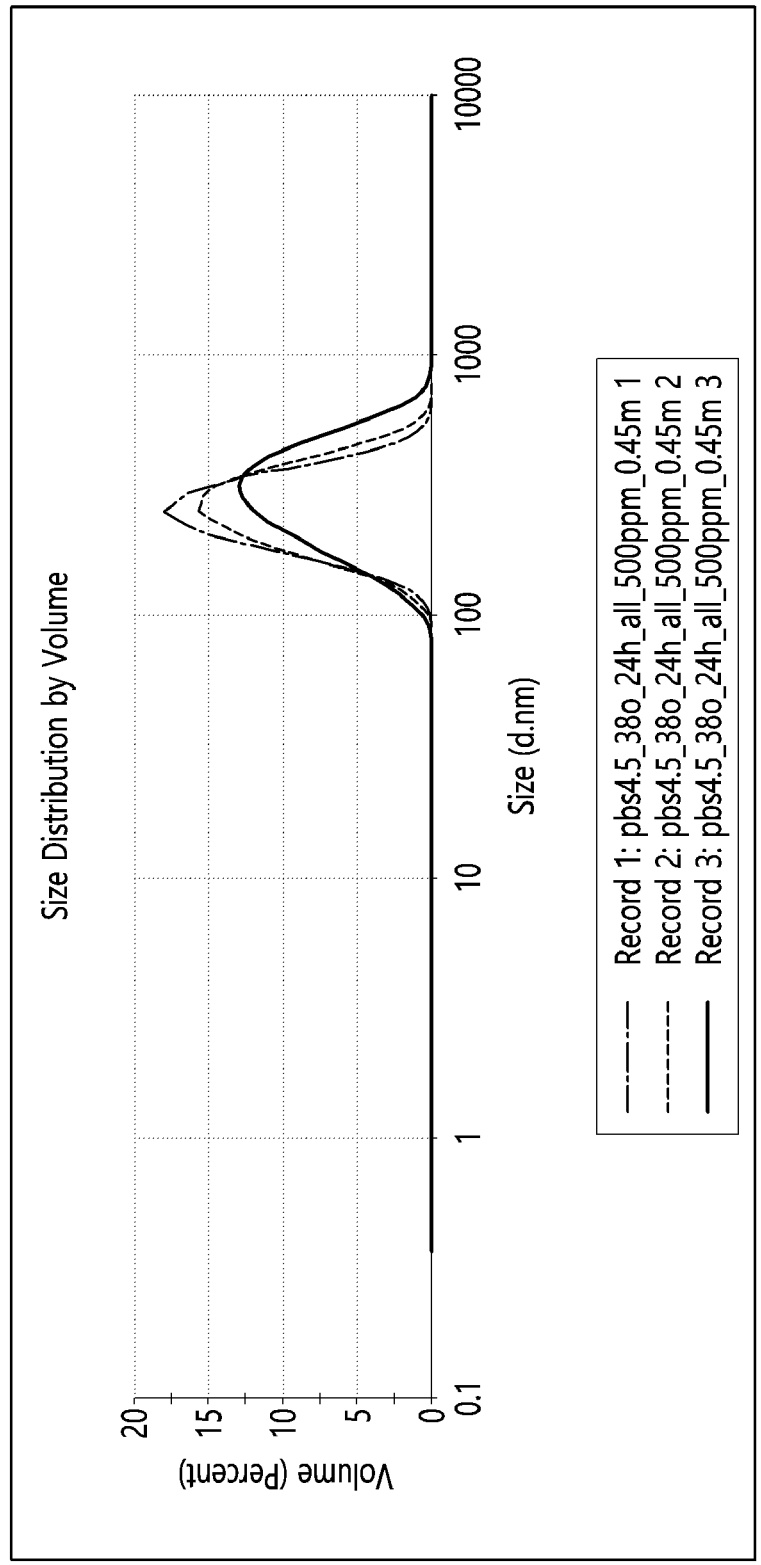
FIG. 17 is a diagram of a particle size of Example 3 (500 ppm).
Figure 18:
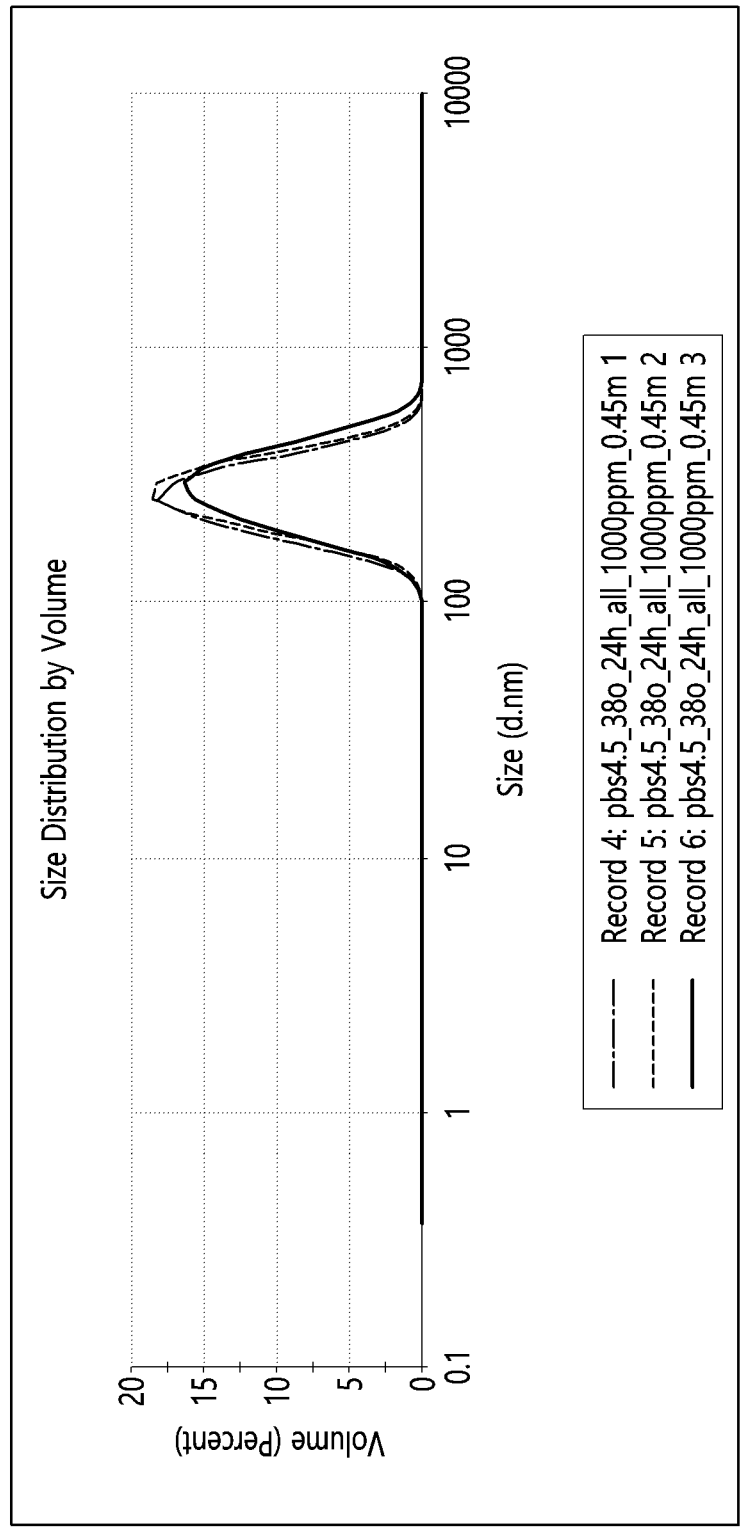
FIG. 18 is a diagram of the particle size of Example 3 (1000 ppm).
Figure 19:
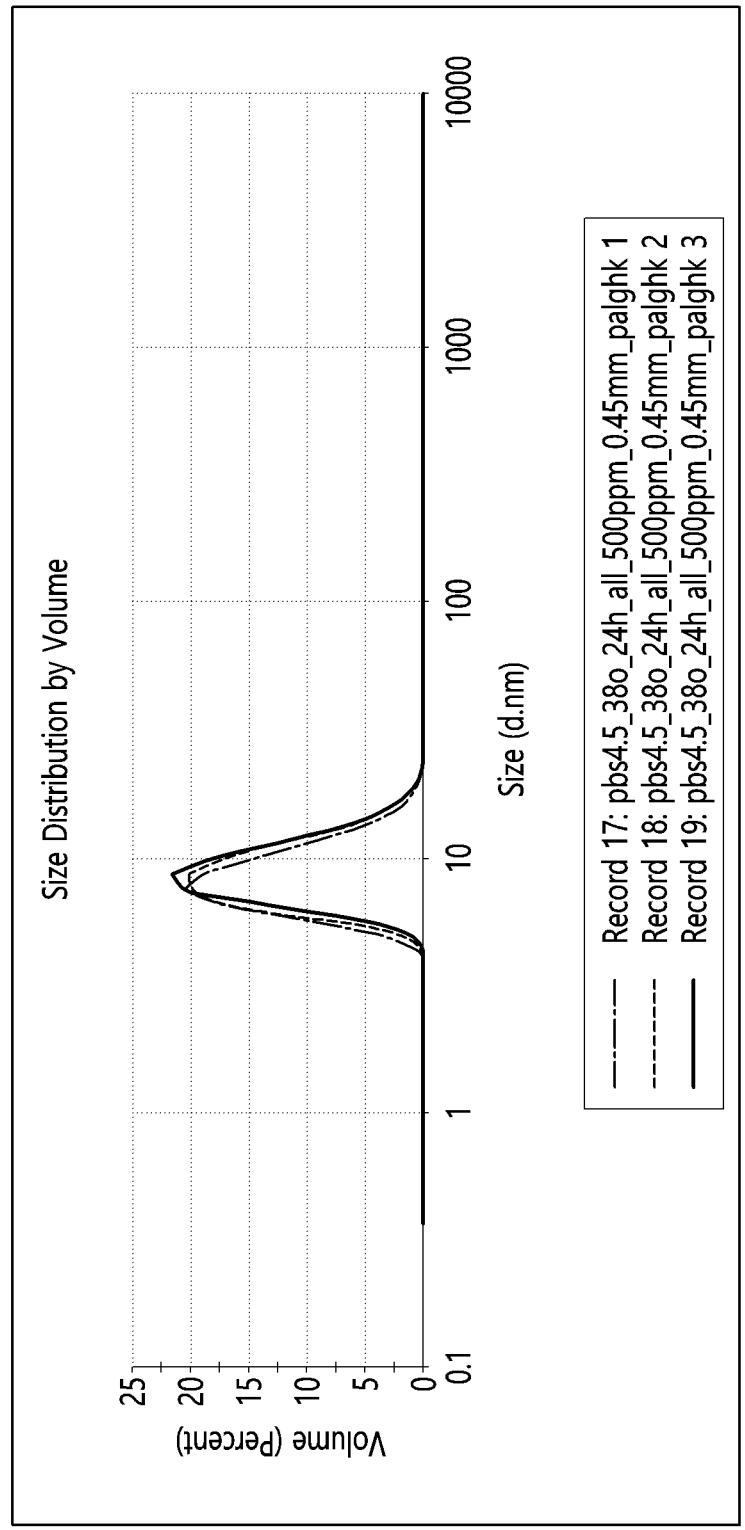
FIG. 19 is a diagram of the particle size of pal-GHK (500 ppm).
Figure 20:
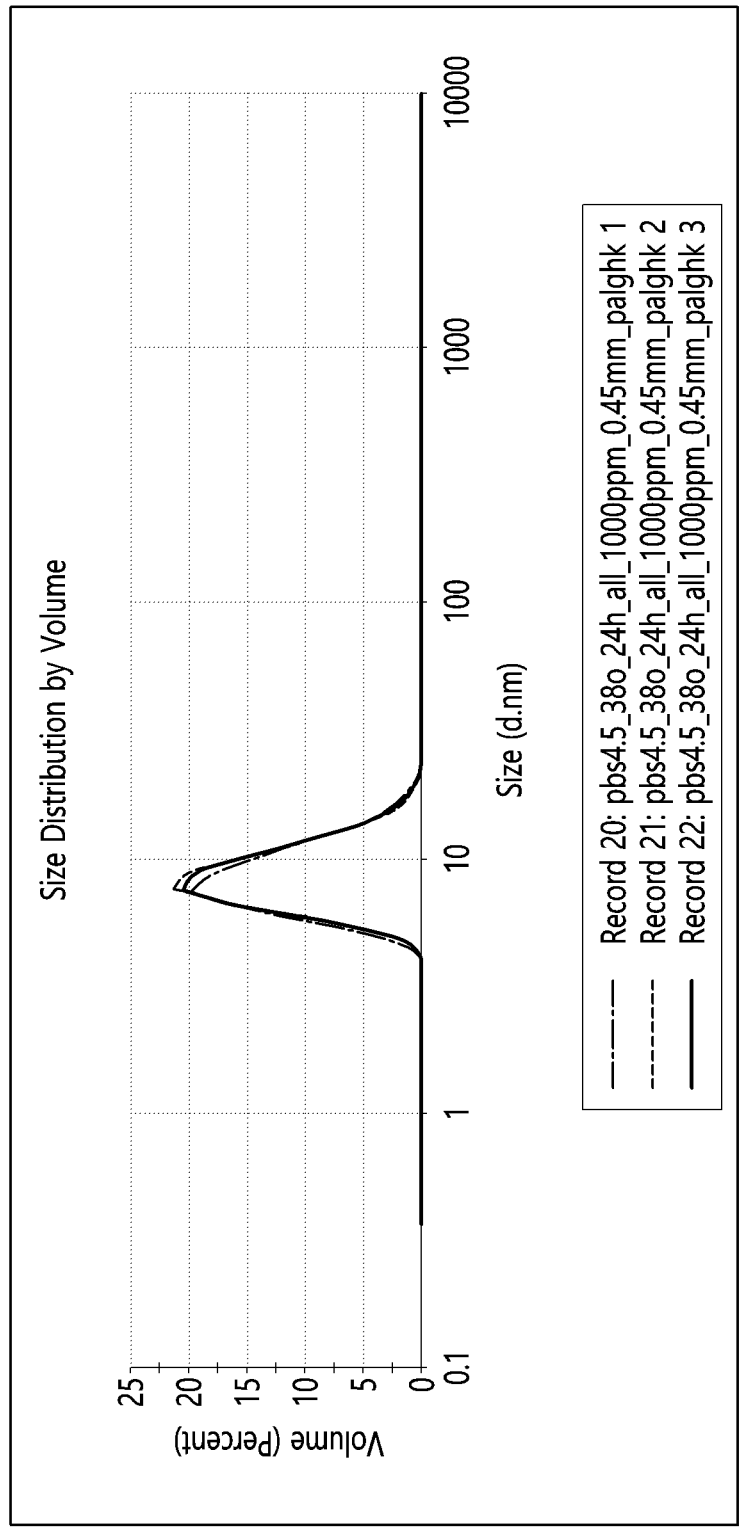
FIG. 20 is a diagram of the particle size of pal-GHK (1000 ppm).

1) Type: In-lens Schottky FE-electron gun
2) Electron detector system: Upper detector r-filter, Built-in, Lower detector
3) EDS (Energy Dispersive Spectrometry): Qualitative/quantitative analysis of ingredients using X-ray The SEM-EDX of the metal phase transformation compound of Example 3 was measured, and the results are illustrated in FIG. 15 and Table 3.

TABLE 3

| Element | Wt % | Wt % Sigma | Atomic % |
|---|---|---|---|
| C | 50.63 | 0.36 | 67.04 |
| N | 14.00 | 0.45 | 15.89 |
| O | 11.28 | 0.20 | 11.22 |
| Zn | 24.09 | 0.22 | 5.86 |
| Total | 100.00 |  | 100.00 |

Experimental Example 3: Dissolution (or Dispersion)

Confirmation Experiment by Difference in Particle Size and Concentration in Weakly Acidic Solvent of Metal Phase Transformation Compound and Peptide (PalGHK)

Experiment Method

1. Evaluation of Particle Size

Instrument: Zetasizer Nano ZS90
dispersant agent: water
dispersant RI: 1.330
cell: disposable cell
runs counts: 20
Temperature: 25° C.

The particle size of the powder was measured by Zetasizer of Malvern Panalytical Ltd. (UK) using electrophoretic light scattering, and the particle size was measured after dispersing the sample in tertiary distilled water using the model name NANO ZS ZS90.

As a result of DLS analysis, the transmitted peptide exhibited an average size of 13.09 nm at 500 ppm and 12.18 nm at 1000 ppm, and as a result of DLS analysis, the transmitted metal phase transformation compound containing the peptide of the present invention exhibited an average size of 247.6 nm at 500 ppm and averaged 256 nm at 1000 ppm. The evaluation results are illustrated in FIGS. 16 to 19.

2. Dispersability Evaluation

PVDF 0.45 μm filter is used

Measurement is performed using HPLC with stirring for 24 hours.

Temperature conditions similar to the temperature inside the body (38° C.) is maintained The solvent is the same as the pH 4.5 buffer, and experiment is performed at 500 or 1000 ppm based on the peptide content of the sample raw material.

Concentration is calculated based on the peptide content (approximately 71%) in the metal compound.

Concentration is calculated based on the peptide content (about 83%) in the peptide (palGHK).

The results obtained by evaluating dispersibility by the above method are listed in Table 4 below.

TABLE 4

| time (hr) | Example3 (500 ppm) (%) | Example 3 (1000 ppm) (%) | palGHK (500 ppm) (%) | palGHK (1000 ppm) (%) |
|---|---|---|---|---|
| 0 | 0 | 0 | 0 | 0 |
| 2 | 23.3 | 20.7 | 21.3 | 18.7 |
| 4 | 30.9 | 36.4 | 27.4 | 27.8 |
| 6 | 38.9 | 47.9 | 37.6 | 33.2 |
| 8 | 54.0 | 61.0 | 39.8 | 42.9 |
| 10 | 56.1 | 66.1 | 37.8 | 47.8 |
| 12 | 56.4 | 66.9 | 35.6 | 47.8 |

As a result of the experiment, the particle size of the peptide decreased at weak acidity (pH 4.5), and the filter transmission of about 35% for 500 ppm and about 47% for 1000 ppm seemed to increase to the highest until 12 hours, but a tendency to decrease thereafter was predicted. On the other hand, the particle size of the metal phase transformation compound containing the peptide of the present invention was decreased at weak acidity (pH 4.5), and the total particle size was decreased up to 12 hours, and the filter transmission of about 56% for 500 ppm and about 66% for 1000 ppm was found to be increased to the highest. In the DLS analysis, when considering that the transmitted peptide appears to have a smaller particle size than that of the permeated metal phase transformation compound of the present invention, whereas the metal phase transformation compound of the present invention has more particles substantially passing through the filter, it is predicted that the efficiency of the metal phase transformation compound of the present invention is more excellent.

Figure 21:
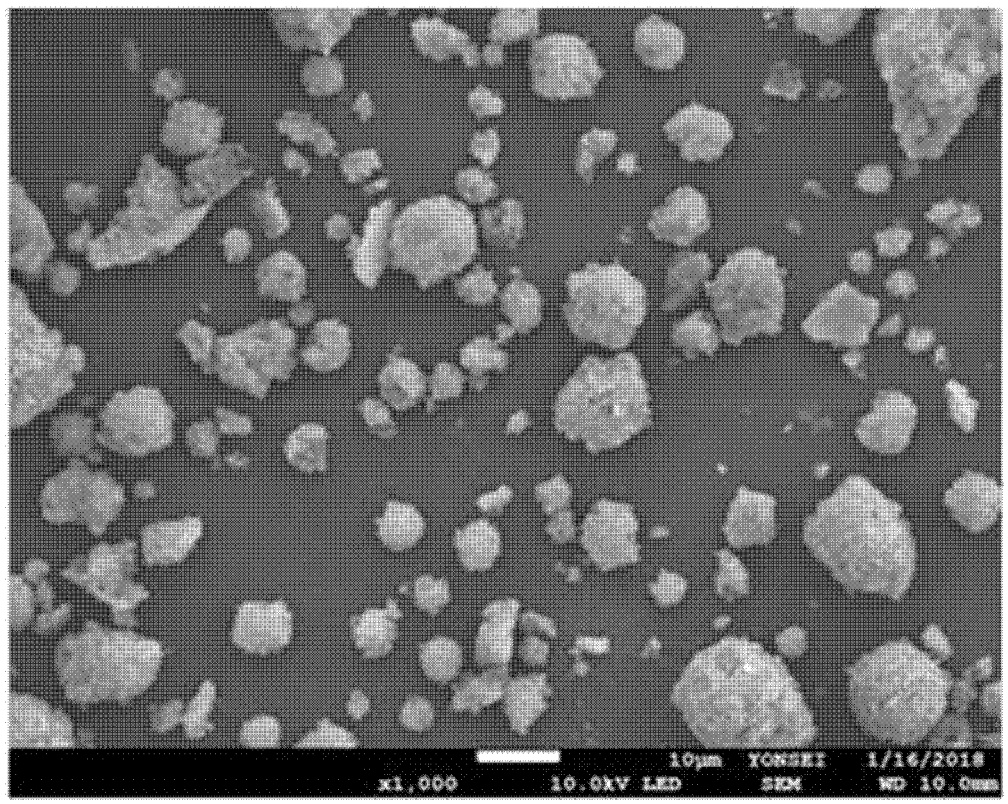
FIG. 21 is an FE-SEM scanning electron microscope photograph of the compound of Example 3 magnified 1000 times.
Figure 22:
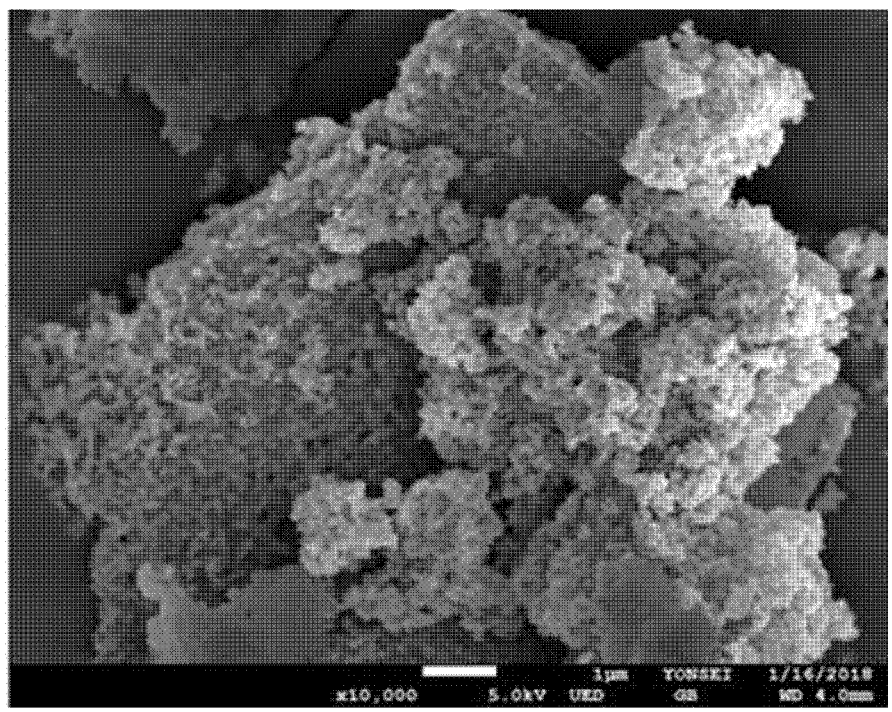
FIG. 22 is an FE-SEM scanning electron microscope photograph of the compound of Example 3 magnified 10000 times.
Figure 23:
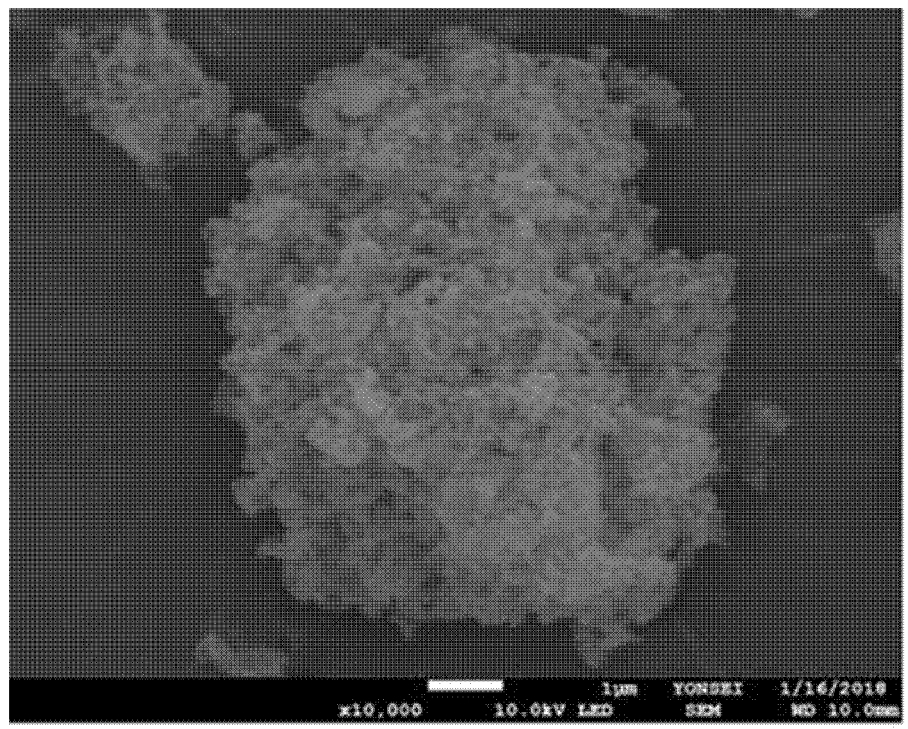
FIG. 23 is an FE-SEM scanning electron microscope photograph of the compound of Example 3 magnified 10000 times
Figure 24:
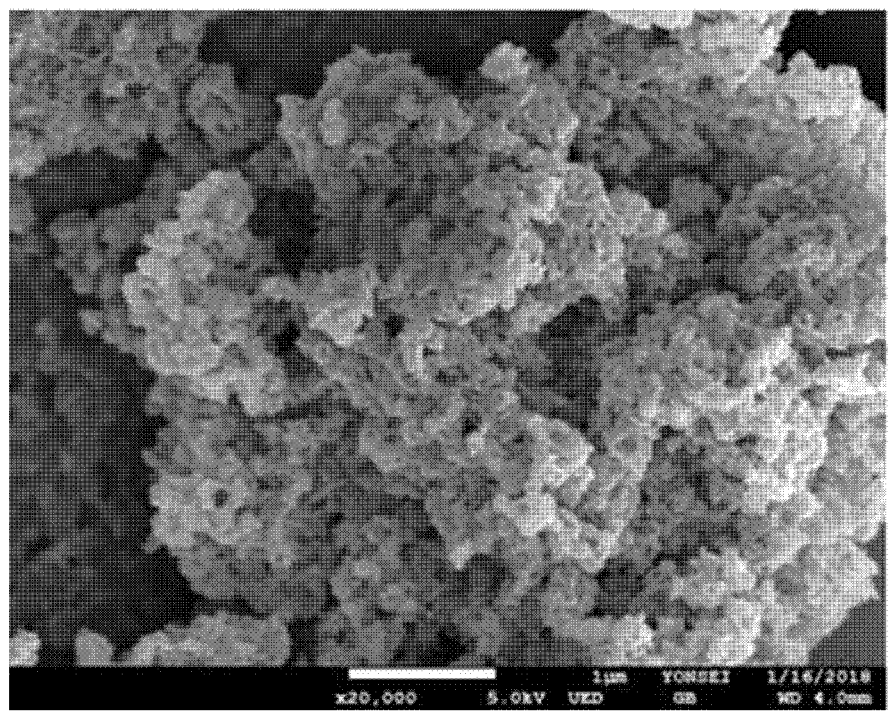
FIG. 24 is an FE-SEM scanning electron microscope photograph of the compound of Example 3 magnified 20000 times.
Figure 25:
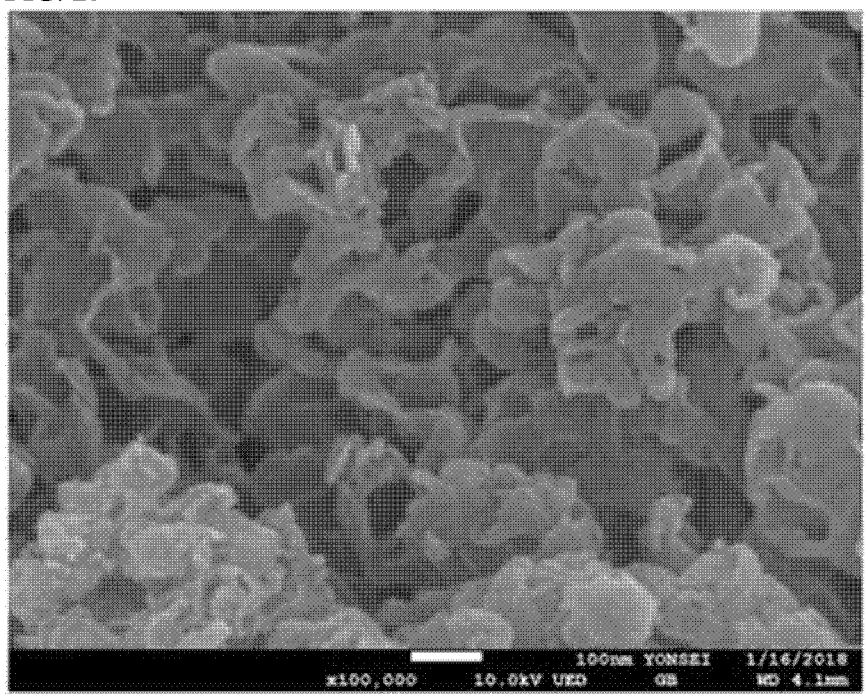
FIG. 25 is an FE-SEM scanning electron microscope photograph of the compound of Example 3 magnified 100000 times.

Experimental Example 4: Evaluation According to FE-SEM Analysis and Field Emission Scanning Electron Microscope Photograph As a result of photographing the powder synthesized according to Example 3 by the field emission scanning electron microscope, it was confirmed that a metal phase transformation compound having a size of several tens of nanometers (nm) to several hundred micrometers (μm) was formed as illustrated in FIG. 21. If magnification is further increased by 10 times based on FIG. 21, particles as illustrated in FIGS. 22 and 23 can be seen. Even looking at FIGS. 22 and 23, it can be seen that the metal phase transformation compound of the present invention is formed by agglomeration of small particles. If magnification is further increased by 20 times based on FIG. 21, it is the same as in FIG. 24, and if magnification of 100 is further increased by 20 times, it is the same as in FIG. 25. In particular, looking at FIG. 25, which is the largest magnification of this metal phase transformation compound, the form in which small particles in a round shape are aggregated can be seen. This is related to the variance experiment previously tested, even if the particle size of the metal phase transformation compound has a size of several tens of microns or more, when the pH-sensitive complex was treated with a 0.45 micrometer (450 nanometer) filter under a specific pH condition, it was possible to see the result of passing more particles, it can be seen that particle size control of the metal phase transformation compound is easy.

Experimental Example 5: Evaluation According to TEM Analysis and Transmission Electron Microscope Photograph This is an electron micrograph of the metal phase transformation compound of Example 3 of the present invention according to a device that generates an electron beam and transmits it through a sample to observe and image the internal/crystal structures of various materials and analyze chemical components.

Instrument Configuration

Electron Gun Type: Schottky Field Emission Gun
Resolution: 0.23 nm (at TEM)/0.19 nm (at STEM)
Magnification: ×20 to ×2.0 M (at TEM)/×100 to ×150 M (at STEM)
Accelerating Voltage: 80/120/200 Kv
Tilt Angle: ±30°

Figure 26:
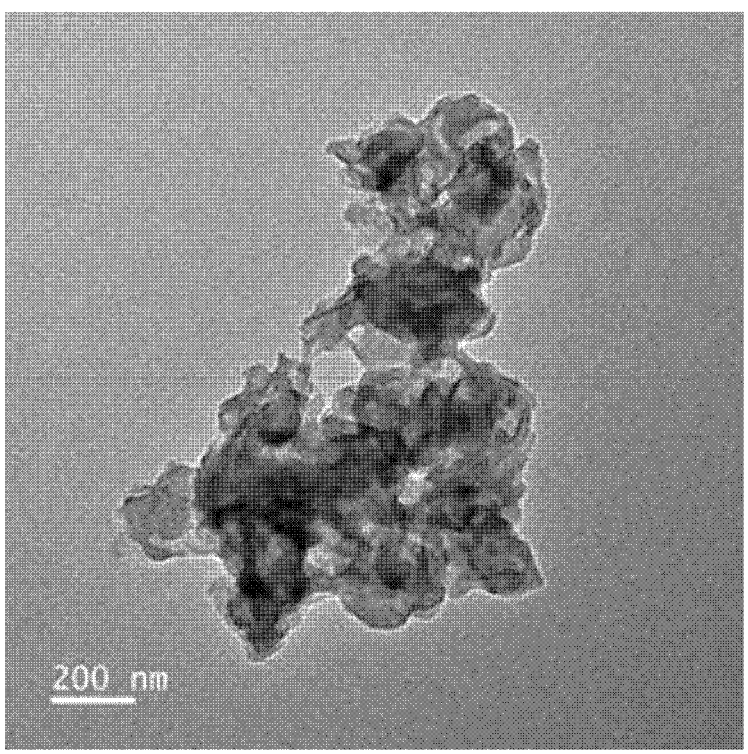
FIGS. 26 to 29 are TEM transmission electron micrograph photographs of Example 3.
Figure 27:
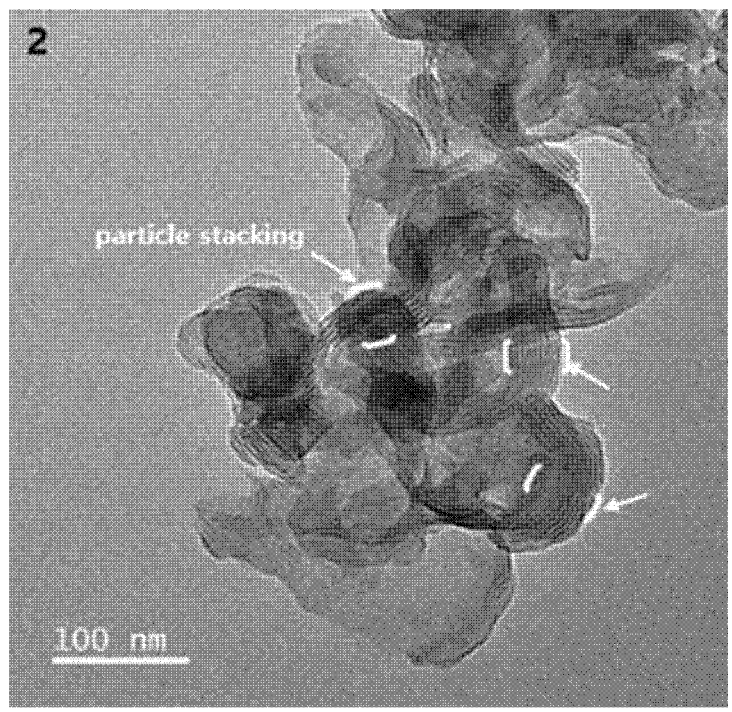
Figure 28:
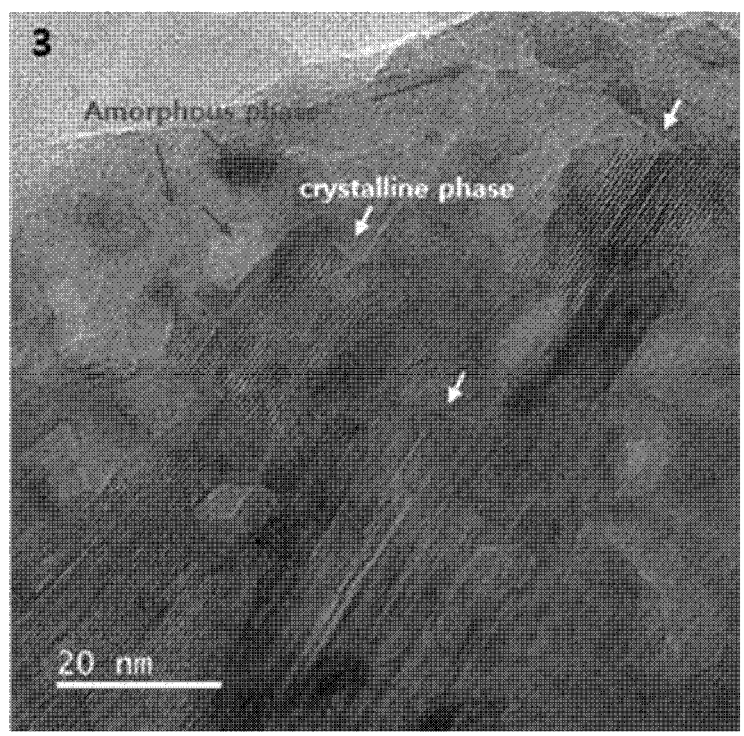
Figure 29:
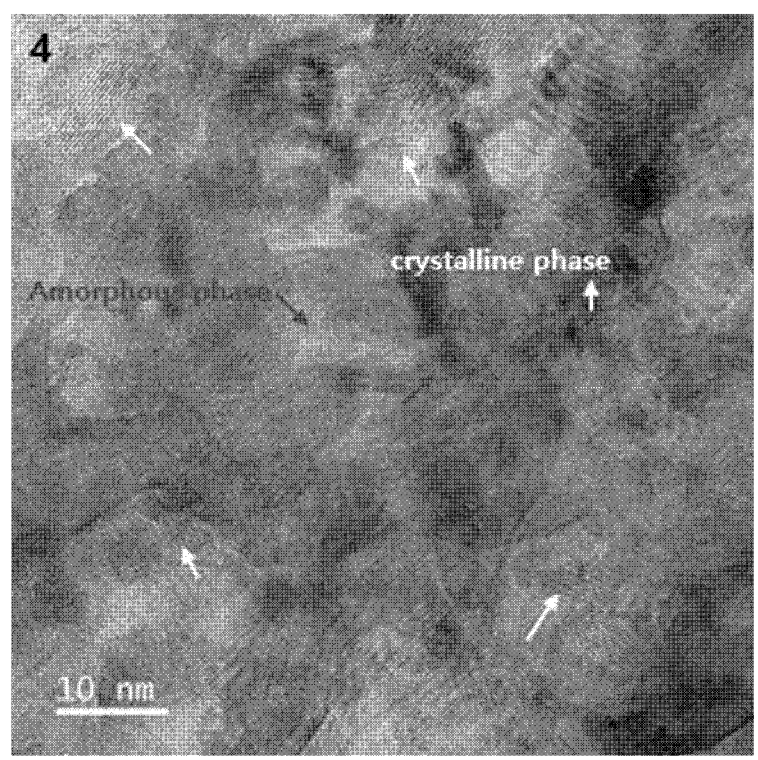

The structure of the metal phase transformation compound synthesized according to Example 3 was measured with the electron microscope, and the results are illustrated in FIGS. 26 to 29. Referring to FIGS. 26 and 27, it can be seen that in the phase change metal compound of the present invention, small particles are gathered to form one large particle. In addition, FIG. 27 illustrates enlarged particles, and it can be seen that small particles are stacked to form particles. In addition, referring to FIGS. 28 and 29 in which the size of the particles is further enlarged, it can be seen that shadows are clearly observed in amorphous trait, and a layered structure or a lattice pattern appears in the crystalline portion. It can be seen that the metal phase transformation compound of the present invention corresponds to a compound in which amorphous form and crystalline form are mixed.

The invention claimed is:

1. A metal phase transformation compound comprising:
   at least one of a metal oxide and a metal hydroxide; and
   peptides containing two to seven amino acids,
   wherein the metal phase transformation compound is represented by Chemical Formula 1, $\{M^{2+}(OH)_y(O)_z\}A_{(2-x')} \cdot nH_2O$     [Chemical Formula 1]

(Wherein Chemical Formula 1,
   $M^{2+}$ is $Mg^{2+}$, $Ca^{2+}$, $Co^{2+}$, $Cu^{2+}$, $Ni^{2+}$, or $Zn^{2+}$,
   A is the peptides,
   x' is a number of 1 or more and less than 2,
   y is a number of 0 or more and 2 or less,
   z is a number of 0 or more and 2 or less,
   y+z does not exceed 2,
   y and z do not have a value of 0 at the same time, and
   n is a number of 0 or more and 10 or less).

2. The metal phase transformation compound of claim 1, wherein the metal phase transformation compound contains 1 to 40% by volume crystalline form and 99 to 60% by volume amorphous form.

3. The metal phase transformation compound of claim 1, wherein, in a powder X-ray diffraction pattern, a peak is widely formed in a range of 15 to 25° in a diffraction angle (2θ).

4. The metal phase transformation compound of claim 1, wherein the powder X-ray diffraction pattern comprises peak values of diffraction angles (2θ)=19±6°, 33±5°, and 59±5°, and comprises one or more peaks within a peak formed in the range of 15 to 25°.

5. The metal phase transformation compound of claim 1, wherein the peptides have PI values of 2 to 12.

6. The metal phase transformation compound of claim 1, wherein the peptides are one or more peptides selected from dipeptide-1 (YR), dipeptide-2 (VW), dipeptide-4 (FW), dipeptide-6 (KV), dipeptide-7 (KT), dipeptide-14 (AT), GH dipeptide (GH), acetyl dipeptide-1 (YR), acetyl dipeptide-1 cetyl Ester (YR), nicotinoyl dipeptide-2 (VW), CP dipeptide (CP), VGE dipeptide (VE), CGE dipeptide (CE), EGE dipeptide (EE), TGE dipeptide (TE), LGE dipeptide (LE), EQ dipeptide (EQ), GR dipeptide (GR), HG dipeptide (HG), PE dipeptide (PE), DE dipeptide (DE), HQ dipeptide (HQ), RS dipeptide (RS), HP dipeptide (HP), carnosine (AH), tripeptide-1 (GHK), tripeptide-3 (GHR), tripeptide-4 (LGD), tripeptide-5 (KVK), tripeptide-6 (GXP), tripeptide-8 (HFR), tripeptide-10 (KDI), RGD peptide (RGD), AHK peptide(AHK), tripeptide-29 (GPX), tripeptide-54 (FTY), biotinoyl tripeptide-1 (GHK), thioctoyl tripeptide-1 (GHK), tripeptide (RFK), HGG peptide(HGG), RKR peptide (RKRM; SEQ ID NO: 1), tetrapeptide-1 (LPTV; SEQ ID NO: 2), tetrapeptide-2 (KDVY; SEQ ID NO: 3), tetrapeptide-3 (KGHK; SEQ ID NO: 4), tetrapeptide-5 (AHSH; SEQ ID NO: 5), tetrapeptide-7 (GQPR; SEQ ID NO: 6), tetrapeptide-9(QDVH; SEQ ID NO: 7), tetrapeptide-11(PPYL; SEQ ID NO: 8), tetrapeptide-15 (YPFF; SEQ ID NO: 9), tetrapeptide-21 (GEKG; SEQ ID NO: 10), tetrapeptide-26 (ELPS; SEQ ID NO: 11), acetyl tetrapeptide-2 (KDVY; SEQ ID NO: 12), acetyl tetrapeptide-3 (KGHK; SEQ ID NO: 13), acetyl tetrapeptide-5 (AHSH; SEQ ID NO: 14), acetyl tetrapeptide-9 (QDVH; SEQ ID NO: 15), acetyl tetrapeptide-11 (PPYL; SEQ ID NO: 16), acetyl tetrapeptide-15 (YPFF; SEQ ID NO: 17), pentapeptide-3 (GPRPA; SEQ ID NO: 18), pentapeptide-4 (KTTKS; SEQ ID NO: 19), pentapeptide-17 (KLAKK; SEQ ID NO: 20), pentapeptide-18 (YAGFL; SEQ ID NO: 21), thioctoyl pentapeptide-4 (KTTKS; SEQ ID NO: 22), hexapeptide-1 (ARHLFW; SEQ ID NO: 23), hexapeptide-2 (FWFKPV; SEQ ID NO: 24), hexapeptide-3 (EEMQRR; SEQ ID NO: 25), hexapeptide-4 (FGHXAF; SEQ ID NO: 26), hexapeptide-5 (FGVXAF; SEQ ID NO: 27), hexapeptide-6 (VEPIPY; SEQ ID NO: 28), hexapeptide-9 (GPQGPQ; SEQ ID NO: 29), hexapeptide-11 (FVAPFP; SEQ ID NO: 30), hexapeptide-12 (VGVAPG; SEQ ID NO: 31), acetyl hexapeptide-3 (EEMQRR; SEQ ID NO: 32), acetyl hexapeptide-8 (EEMQRR; SEQ ID NO: 33), heptapeptide-6 (HWAWFK; SEQ ID NO: 34), cysteine peptide (RFAACAA; SEQ ID NO: 35), palmitoyl dipeptide-6 (KV), palmitoyl dipeptide-7 (KT), azelaoyl tripeptide-1 (GHK), palmitoyl-tripeptide-3 (GHR), palmitoyl tripeptide-5 (KVK), palmitoyl tripeptide-1 (GHK), palmitoyl tripeptide-5 (KVK), palmitoyl tripeptide (RFK), myristoyl tripeptide-1 (GHK), palmitoyl tripeptide-4 (LGD), palmitoyl tripeptide-8 (HFR), palmitoyl tetrapeptide-7 (GQPR; SEQ ID NO: 36), myristoyl pentapeptide-17 (KLAKK; SEQ ID NO: 37), palmitoyl pentapeptide-4 (KTTKS; SEQ ID NO: 38), palmitoyl pentapeptide-17 (KLAKK; SEQ ID NO: 39), myristoyl hexapeptide-12 (VGVAPG; SEQ ID NO: 40), and palmitoyl hexapeptide-12 (VGVAPG; SEQ ID NO: 40).

7. The metal phase transformation compound of claim 1, wherein the metal phase transformation compound contains 20 to 80% by weight peptide within one unit cell.

8. The metal phase transformation compound of claim 1, wherein the metal phase transformation compound contains 20 to 80% by weight peptide within one unit cell and 10 to 35% by weight metal.

\* \* \* \* \*